(12) United States Patent
Fox et al.

(10) Patent No.: US 7,087,008 B2
(45) Date of Patent: Aug. 8, 2006

(54) APPARATUS AND METHODS FOR DELIVERY OF TRANSCRANIAL MAGNETIC STIMULATION

(75) Inventors: Peter Fox, San Antonio, TX (US); Jack Lancaster, San Antonio, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 352 days.

(21) Appl. No.: 10/138,543

(22) Filed: May 3, 2002

(65) Prior Publication Data

US 2003/0050527 A1     Mar. 13, 2003

Related U.S. Application Data

(60) Provisional application No. 60/288,670, filed on May 4, 2001.

(51) Int. Cl.
*A61N 1/00* (2006.01)

(52) U.S. Cl. ...................................................... 600/13
(58) Field of Classification Search .................. 600/13, 600/14, 427, 429, 407, 417, 544; 128/897, 128/899; 378/20; 606/130, 1–19, 49–52; 901/16, 41, 6, 43, 15; 228/102; 91/530, 91/34, 48, 519; 118/302, 323, 697; 427/265, 427/427.2, 429; 700/248, 262, 245; 318/368.15, 318/368.17, 573; 482/901, 4; 604/425; 601/33

See application file for complete search history.

(56) References Cited

U.S. PATENT DOCUMENTS

| | | | |
|---|---|---|---|
| 4,864,966 A * | 9/1989 | Anderson et al. ........... | 427/265 |
| 4,937,759 A * | 6/1990 | Vold ............................ | 700/262 |
| 4,940,453 A | 7/1990 | Cadwell ....................... | 600/13 |
| 4,990,839 A * | 2/1991 | Schonlau ..................... | 700/248 |
| 5,047,005 A * | 9/1991 | Cadwell ....................... | 600/13 |
| 5,078,140 A * | 1/1992 | Kwoh .......................... | 600/417 |
| 5,116,304 A | 5/1992 | Cadwell ....................... | 600/13 |
| 5,236,432 A | 8/1993 | Matsen, III et al. .......... | 606/88 |
| 5,427,097 A * | 6/1995 | Depp ........................... | 600/427 |
| 5,466,213 A * | 11/1995 | Hogan et al. ................. | 601/33 |
| 5,697,285 A * | 12/1997 | Nappi et al. ................. | 91/519 |
| 5,725,471 A | 3/1998 | Davey et al. ................. | 600/13 |
| 5,806,518 A | 9/1998 | Mittelstadt ............... | 128/653.1 |
| 6,013,997 A * | 1/2000 | Heideman et al. .......... | 318/648 |

(Continued)

FOREIGN PATENT DOCUMENTS

DE     199 09 587 A 1     7/1998

(Continued)

OTHER PUBLICATIONS

PCT/US02/14157 International Preliminary Examination Report Mailed Jul. 8, 2003.

(Continued)

*Primary Examiner*—John P. Lacyk
(74) *Attorney, Agent, or Firm*—Trop, Pruner & Hu, P.C.

(57) ABSTRACT

Disclosed are apparatus and methods for delivery of transcranial magnetic stimulation. The apparatus includes a TMS coil which when energized generates an electric field substantially parallel to a long axis of the coil and substantially normal to a surface of the coil. Furthermore disclosed an apparatus for delivery of TMS in which a coil is adapted to a robotic member for computer-aided control and delivery. Further disclosed are methods of TMS planning and delivery in which subject images are utilized to plan, position and orient the TMS coil for precise delivery. Disclosed also are TMS coils having unique designs to better focus and direct magnetic stimulation.

25 Claims, 17 Drawing Sheets

U.S. PATENT DOCUMENTS

| | | | | |
|---|---|---|---|---|
| 6,035,228 | A * | 3/2000 | Yanof et al. | 600/429 |
| 6,048,302 | A * | 4/2000 | Markoll | 600/13 |
| 6,076,008 | A | 6/2000 | Bucholz | 600/427 |
| 6,086,525 | A | 7/2000 | Davey et al. | 600/13 |
| 6,099,459 | A * | 8/2000 | Jacobson | 600/13 |
| 6,132,361 | A | 10/2000 | Epstein et al. | 600/13 |
| 6,179,770 | B1 | 1/2001 | Mould | 600/13 |
| 6,179,771 | B1 | 1/2001 | Mueller | 600/13 |
| 6,198,958 | B1 | 3/2001 | Ives et al. | 600/411 |
| 6,212,419 | B1 * | 4/2001 | Blume et al. | 600/407 |
| 6,266,556 | B1 * | 7/2001 | Ives et al. | 600/544 |
| 6,330,467 | B1 * | 12/2001 | Creighton et al. | 600/407 |
| 6,366,814 | B1 | 4/2002 | Boveja et al. | 607/45 |
| 6,459,924 | B1 * | 10/2002 | Creighton et al. | 600/427 |
| 6,585,746 | B1 | 7/2003 | Gildenberg | 606/187 |
| 6,783,524 | B1 * | 8/2004 | Anderson et al. | 606/28 |

FOREIGN PATENT DOCUMENTS

| | | | |
|---|---|---|---|
| GB | 2 261 820 A | 6/1993 | |

OTHER PUBLICATIONS

PCT/US02/14157 International Search Report Mailed Apr. 7, 2003.

Wasserman et al., Locating the Motor Cortex on the MRI with Transcranial Magnetic Stimulation (Feb. 1996); NeuroImage, vol. 3, No. 1: pp. 1-9.

Paus et al., Transcranial Magnetic Stimulation during Positron Emission Tomography: A New Method for Studying Connectivity of the Human Cerebral Cortex (May 1, 1997); The Journal of Neuroscience, vol. 17, No. 9: pp. 3178-3184.

Krings et al., Stereotactic Transcranial Magnetic Stimulation: Correlation with Direct Electrical Cortical Stimulation (Dec. 1997); Neurosurgery, vol. 41, No. 6: pp. 1319-1326.

Paus et al., Transcranial Magnetic Stimulation During PET: Reaching and Verifying the Target Site (1998); Hum. Brain Map, vol. 6, No. 5-6: pp. 399-402.

Paus, Imaging the Brain Before, During, and After Transcranial Magnetic Stimulation (Feb. 1999); Neuropsychologia, vol. 37, No. 2: pp.. 219-224.

Boroojerdi et al., Localization of the Motor Hand Area Using Transcranial Magnetic Stimulation and Functional Magnetic Resonance Imaging (Apr. 1999); Clin. Neurophysiol vol. 110, No. 4: pp. 699-704.

NEUROMATE—Integrated Surgical Systems (http://www.robodoc.com/eng/neuromate.html).

Davey, Magnetic Stimulation Coil and Circuit Design (Nov. 2000); IEEE Transactions on Biomedical Engineering, vol. 47, No. 11: pp. 1493-1499.

Hsu et al., A 3-D Differential Coil Design for Localized Magnetic Stimulation (Oct. 2001); IEEE Transactions on Biomedical Engineering, vol. 48, No. 10: pp. 1162-1168.

Weh-Hau Lin et al., Magnetic Coil Design Considerations for Functional Magnetic Stimulation (May 2000); IEEE Transactions on Biomedical Engineering, vol. 47, No. 5: pp. 600-610.

Ruohonen et al., Functional Magnetic Stimulation: Theory and Coil Optimization (1998); Bioelectrochemistry and Bioenergietics 47: pp. 213-219.

Turner, A Target Field Approach to Optimal Coil Design (1986); The Institute of Physics 19: L147-L151.

Turner, Minimum Inductance Coils (1988); IOP Publishing Ltd.: pp. 948-952.

Mouchawar et al., Guidelines for Energy-Efficient Coils: Coils Designed for Magnetic Stimulation of the Heart (1991); Magnetic Motor Stimulation: Basic Principles and Clinical Experience (EEG Supp.. 43): pp. 255-267.

Caldwell, Optimizing Magnetic Stimulator Design (1991); Magnetic Motor Stimulation: Basic Principles and Clinical Experience (EEG Supp.. 43): pp. 238-248.

Martens et al., Insertable Biplanar Gradient Coils for Magnetic Resonance Imaging (1991); American Institute of Physics, Rev. Sci. Instrum. vol. 62, No. 11: pp. 2639-2645.

Ruohonen et al., Coil Design for Real and Sham Transcranial Magnetic Stimulation (Jan. 2000); IEEE Transactions on Biomedical Engineering, vol. 47, No. 2. pp. 145-148.

Guggisberg et al., Motor evoked potentials from masseter muscle induced by Transcranial magnetic stimulation of the pyramidal tract: the importance of coil orientation (Dec. 2001), Clin Neurophysiol. 2001; 112(12), pp. 2312-2319.

Herwig et al., The navigation to transcranial magnetic stimulation (Nov. 30, 2001), Psychiatry Res.; 108(2); pp. 123-131.

Supplementary Partial European Search Report for EPO Application No. 02724022.5-2305; Mailed Nov. 10, 2005.

Narayama et al. "Use of Neurosurgical Robot for Aiming and Holding in Cortical TMS Experiments", NEUROIMAGE. vol. 11, No. 5, 2000. p. S471.

Traad, Monique. "A Quantitative Positioning Device For Transcranial Magnetic Stimulation". Engineering In Medicine and biology Society, 1990. Proceedings of the Twelfth Annual International Conference of the IEEE. Philadelphia, PA, Nov. 1-4, 1990. p. 2246.

Ilmoniemi et al., "Transcranial Magnetic Stimulation—A New Tool for Functional Imaging of the Brain". Critical Reviews in Biomedical Engineering, CRC Press. vol. 27, No. 3-5, 1999, pp. 241-284.

Supplementary Partial European Search Report for EPO Application No. 02724022.5-2305; Mailed Jul. 11, 2005.

* cited by examiner

APPARATUS AND METHODS FOR DELIVERY OF TRANSCRANIAL MAGNETIC STIMULATION

This application claims priority to the U.S. Provisional Application No. 60/288,670 filed on May 4, 2001 in the name Peter Fox and Jack Lancaster entitled APPARATUS AND METHODS FOR DELIVERY OF TRANSCRANIAL MAGNETIC STIMULATION.

This invention was made with government support under contract number 5R01MH60246-02. The government has certain rights in this invention.

BACKGROUND OF THE INVENTION

1. Field of the Invention

The present invention is directed to apparatus and methods particularly suitable for precise aiming and delivery of magnetic stimulation, and more specifically, transcranial magnetic stimulation.

2. Description of the Related Art

Transcranial magnetic stimulation ("TMS")is a means of repetitively stimulating the human brain through an intact scalp and skull, i.e., non-invasively. TMS is delivered by passing a brief (200 microsecond), strong (10,000 volts, 6,000 amps) electrical current through a coil of wire (a TMS stimulator) placed adjacent to the head. The passage of electrical current induces a strong (2 Tesla) magnetic field which, in turn, induces electrical currents in nearby tissues. In the case of nerve cells, if the induced current is sufficiently intense and properly oriented, it will result in synchronized depolarization of a localized group of neurons (i.e., neuronal "firing"). Initially, magnetic stimulation was used only for peripheral nerves, in which instance it is affecting nerve fibers rather than neuronal cell bodies. More recently (Barker et al., 1985), magnetic stimulation has shown to be able to depolarize neurons in the brain. The cellular element of the brain being affected by TMS was assumed, but not proven, to be fibers rather than neuronal cell bodies.

TMS has several present and potential applications, in the domains of basic neuroscience research and of the treatment of brain disorders. Applications for neuroscience research include, for example: imaging brain connectivity (e.g., Fox et al., 1997); establishing inter-regional and inter-hemispheric conduction times (e.g., Meyer et al., 1995); testing the function of specific brain areas by means of transient functional disruptions, so-called "virtual lesions" (e.g., Shipley & Zeki, 1995); and, studying the modification of synaptic efficacy induced by repetitive stimulation, termed LTP (long-term potentiation) and LTD (long-term depression). Potential clinical applications include, for example: pre-operative mapping, e.g., of language related brain areas (Epstein (et al., 1996); testing for neuronal conduction delays due to dysmyelinating disorders; and, treating brain disorders by selective modification (up or down regulation) of the synaptic efficacy of pathways (i.e., by inducing LTP and LTD; Wang, Wang and Scheich, 1996).

At present, TMS delivery is crude. The TMS effector or stimulator (commonly referred to as a "TMS coil") is a wire-wound coil, typically shaped like a "B." The B-shaped coil is placed against the scalp and held in place by a human operator. For the primary motor cortex and primary visual cortex (small sections of the total brain surface), proper positioning is established by the elicited response: muscle contractions when stimulating the primary motor cortex; illusory lights (phosphenes) when stimulating the primary visual cortex. In both of these areas, the effects are very sensitive to coil position and orientation.

For brain regions in which proper positioning cannot be determined by the induced effects (i.e., muscle contractions or subjective experience), position is generally determined by reference to a traditional pattern used for placement of EEG electrodes (10/20 system). The 10/20 system is based on scalp/skull landmarks which do not bear a reliable relationship to the functional anatomy of the brain. Further, when using the 10/20 system, there has been no strategy enunciated for determining proper orientation of the coil. Thus, a reliable method for determining the proper position and orientation of TMS coil placement for brain areas lacking immediately observable feedback is needed.

Application of TMS during radionuclide imaging (using positron-emission tomography ("PET")or single photon emission tomography ("SPECT")) has two important uses. First, radionuclide imaging can be used to monitor the induced response, determining precise location and quantifying response magnitude. This is extremely important for testing aiming algorithms and for determining the effect of stimulation parameters, such as intensity, rate, duration and the like. Second, an important use of TMS is to map brain connectivity using radionuclide imaging. For both of these applications, hand-held TMS delivery is inappropriate, for at least three reasons. First, hand-held delivery is unsafe, unnecessarily exposing the experimenter to the radiation used for imaging. Second, hand-held delivery is positionally unstable, degrading image quality by small movements of the holder. Third, hand-held delivery is intrinsically inaccurate and imprecise.

Further, current coil designs for delivery of TMS have been mainly intuitive and somewhat crude. Typical coil designs consist of two loop figure eight type coils, for peripheral nerve and brain stimulation, four loop coils for peripheral nerve stimulation, and variations in angles of these. While attention is paid to coil inductance, it is only for simple circuits that this may be easily calculated.

The target field method has been used to produce minimum inductance cylindrical gradient coils for MRI (Turner, 1986) and has been adapted for bi-planar coils (Martens et al., 1991). Minimum power designs have also been presented (Bowtell et al.). However, such design methods have not been applied to the design of magnetic stimulation coils.

Various combinations of circular or rectangular coil shapes have been designed. Figure eight type designs appear to be the most common. Further, B-shaped and slinky-type coils have also been designed (Cadwell; Lin et al.). Sections of toroids (Davey, Epstein, Carbunaru) with magnetically permeable cores are also known, and appear to be an efficient design. However, none of these provide an extremely focused field penetration. Two and four wing coils with a straight section joined with curves for peripheral nerve stimulation have been designed. (Ruohonen et al.) However, these designs are largely limited by intuition.

Thus, fundamental limitations on the utility of TMS for research and treatment include a lack of methods for precise, automated aiming (positioning and orienting) and safe, rigid (i.e., non-human) holding of the TMS stimulator, as well as the poor suitability of present coils for TMS.

SUMMARY OF THE INVENTION

The present invention enhances the precision and ease with which TMS may be used for the diagnosis and treatment of neurological and psychiatric disorders and for neuroscience research. In certain embodiments, these benefits may be accomplished via use of specifically shaped TMS stimulators having certain properties. In certain embodiments, a robot, such as a neurosurgical robot, may be used to deliver TMS. The present invention also includes algorithms for treatment planning and treatment delivery, including: algorithms for rapidly modeling the 3-D electric field created in the brain by a TMS coil at any external location; cortical surface modeling (extraction and visualization); scalar product (electric-field vector times cortical-surface vector) computation and visualization; and merging of functional images, structural images and treatment-planning models (surfaces & fields).

The present invention further includes treatment-delivery tools such as frameless registration of head, brain image, and robot; fully automated robotic positioning of the TMS coil; robotic sensing of TMS orientation (about a manually operated tool-rotation axis); hardware extensions including a passive digitizing arm; a TMS tool mount; a passive tool-rotation axis with an orientation sensor; and a general-purpose mobile cart.

Additionally, inventive methods enhance the precision and ease with which TMS may be used for neuroscience research and for the diagnosis and treatment of neurological and psychiatric disorders.

The inventors have determined that the biological efficacy of transcranial magnetic stimulation applied to cerebrum can be estimated at any point as the scalar product of the induced electrical field (E, a vector) and a unit vector aligned parallel to the cortical columns. The unit vector is estimated as a normal (i.e., perpendicular) the cortical surface, as this is the known orientation of cortical columns. The biological efficacy of a TMS E field, then, is calculated using equation 1.

$$\text{Biological efficacy} = |E| \cos \theta \quad [1]$$

where $\theta$ is the angle between E and the unit normal vector. This Cortical Column Cosine Aiming Principle ("CCCAP" or "CAPS" or "aiming principle")is based on the inventors' determination that the cortical column is the biological unit of the brain with the lowest threshold for TMS excitation and the well-established neuro-anatomical principle that the cortical columns are oriented at a right angle to the cortical surface. Thus, maximum biological efficacy of a cortical region of interest occurs where the induced E field is parallel to the direction of the cortical columns, i.e., normal to the cortical surface.

The CCCAP includes the following principles: (1) surface grey matter (the cortex) is preferentially or exclusively activated; axons in the sub-cortical white matter are minimally activated by the TMS-induced E-field, but will conduct action potentials initiated in cortex by TMS; (2) cortical grey matter will be most effectively activated by an E-field oriented parallel to the columnar organization of the cortex; (3) the response magnitude at any cortical location is a function of the magnitude of the E-field parallel to the cortical columns; (4) cortex is preferentially (but not exclusively) activated by orthodromic E-fields, passing from the pial surface, through the soma, to the sub-cortex; antidromic E-fields, passing toward the pial surface will be less effective but not ineffective; and (5) the orientation of the cortical columns is macroscopically estimated as the normal to the true cortical surface. Of the five aiming principles, the first two (particularly the second) are strongly at odds with current opinion and practice in the TMS community. It is to be understood that a true cortical surface is one derived from an anatomical image with sufficient spatial resolution and image contrast to define the cortical-subcortical or cortical-CSF border. Simplified (e.g., spherical) models or generalized models of the cortex which do not define the true cortical surface may not accurately model the orientation of the cortical columns.

FIG. 1 is a cross-sectional view of a subject's head 5 with a B-shaped coil 10 positioned thereabove. As shown, the head includes the scalp and skull 5, the cerebral cortex or grey matter 15, cerebrospinal fluid (CSF) 20, and white matter 25. Where the cortex is concave, folding inwardly away from the scalp and skull, it is termed a sulcus 35 (pl. sucli). For present modelng purposes, the most important components of the cortex are the vertical neurons 40, which are oriented perpendicular to the brain's cortical surface (i.e., perpendicular to the interface between cortex 15 and CSF 20). The vertical neurons collectively form the cortical columns (not shown), which are the dominant anatomical and physiological features of cerebral cortex (at the microscopic level), being present in all regions of cortex in all mamallian species. (Only a few vertical neurons are illustrated in FIG. 1).

In FIG. 1, the TMS coil 10 is positioned and oriented to create an induced E-field that is perpendicular to the brain cortical surface (and parallel to the vertical neurons) in the sulcus (C), but parallel to the cortical surface (and perpendicular to the vertical neurons) at the crown of the gyrus (A). The magnitude of the E field is weaker at C than at A, because the distance from the surface of the TMS coil 10 is greater at C than at A. Relative to the orientation of the vertical neurons forming the cortical columns the E field can be decomposed into vertical (Ev) and horizontal (Eh) components, which are parallel to the vertical neurons and horizontal fibers, respectively. By Principal (2), activation at any cortical site is a function of Ev with negligible Eh effect. Thus, E has no effect (no Ev component) where E is perpendicular to the column (A); intermediate effects for intermediate relative orientations (B); and maximal effect where E is parallel to the column (C).

In FIG. 1, the TMS coil 10 is positioned and oriented to create an induced E-field that is perpendicular to the brain cortical surface (and parallel to the vertical neurons) in the sulcus (C), but parallel to the cortical surface (and perpendicular to the vertical neurons) at the crown of the gyrus (A). The magnitude of the E field is weaker at C than at A, because the distance from the surface of the TMS coil 10 is greater at C than at A. Relative to the orientation of the vertical neurons forming the cortical columns the E field can be decomposed into vertical ($E_v$) and horizontal ($E_h$) components, which are parallel to the vertical neurons and horizontal fibers, respectively. By Principal (2), activation at any cortical site is a function of $E_v$ with negligible $E_h$ effect. Thus, E has no effect (no $E_v$ component) where E is perpendicular to the column (A); intermediate effects for intermediate relative orientations (B); and maximal effect where E is parallel to the column (C).

Prior art (Brasil-Neto et. al 1992; Mills et al., 1992) has empirically demonstrated that coil orientation computed in the manner just described is optimal for one brain area (the primary motor cortex), but provided a rationale not applicable to brain regions other than primary motor cortex and inconsistent with the above explanation.

In an example embodiment, the CCCAP may be used to allow the cortical excitation effects of TMS to be computed in advance for any position and orientation, thereby enabling computer-aided aiming of TMS. However, in other embodiments, the CCCAP may be used for manual aiming and orienting. The CCCAP may also be used to normalize (correct) observed biological effects for the angle of intersection with the cortex, when aiming is done conventionally (i.e., not with CCCAP) but images are obtained showing the relationship between the TMS coil and the cortical surface.

In an example method, image-guided, computer-aided implementation of the CCCAP for TMS delivery may be effected in accordance with the following steps. First, an imaging stage is performed, in which a high-resolution, anatomical image (e.g., a 3D T1-weighted image) of the subject's head is obtained. Preferably, sufficient grey-white contrast is obtained to allow detailed cortical-surface segmentation. Next, a functional image (either functional MRI or PET, for example) data set is obtained during conditions (task/control pair) which selectively activate the cortical region of interest (e.g., repetitive hand movement to activate the supplementary motor area).

Next, a modeling stage is performed to identify surfaces within the anatomical and functional images, to be used for registration of the functional and anatomical images to one another and, subsequently, to the patient. In the anatomical image (e.g., an anatomical MRI), the scalp surface and the brain's cortical surface are segmented and modeled as polygon-mesh surfaces. The brain-surface is modeled at high-resolution, to provide an accurate, detailed representation of the interface between cerebrospinal fluid (CSF) and cortical grey matter, as this is critical for establishing the orientation of the cortical columns. Anatomical surface extraction and modeling is done in a manner keeping both surface models (scalp and brain) in register with the original image and, thereby, with one another. In the functional image (either PET or fMRI), the brain surface is segmented and modeled as a polygon mesh surface (but with less detail than the model derived from the anatomical image) and the targeted site is identified. The two brain surface models (anatomical-image-derived and functional-image-derived) are co-registered, thereby bringing the target site in register with the two MRI-derived cortical surface models: brain and scalp. This comprises a conjoined functional/anatomical model.

Then, a 3-D model of the TMS-coil's physical surface and the 3-D E-field induced by the TMS coil is created, and this TMS coil-surface/E-field model is superimposed on the conjoined functional/anatomical model. The TMS coil-surface/E-field model is positioned and oriented so as to obtain maximum biological efficacy (as defined by the CCCAP) at the target point, while keeping the coil surface outside the scalp surface. The position and orientation of the TMS coil-surface relative to the conjoined functional/anatomical model may then be stored for subsequent use.

In an example embodiment, this data may be used to perform TMS delivery in accordance with the following. First, the subject is placed in the treatment position and the head immobilized, for example, using a thermoplastic mask (Fox et al., 1985). With the subject in the treatment position, a 3-D digitizer (e.g., a passive arm digitizer) may be used to collect a series of points on the scalp surface. These points are used to create a model of the scalp surface in the subject's current head position. This model is registered to the conjoined functional/anatomical model previously created, using a rapid, surface matching algorithm, such as a convex hull algorithm (Lancaster et al., 1999). The manual digitizer may again be used to collect a set of specific reference points on the surface of the TMS coil, which may be mounted on a multi-joint, calibrated armature, either passive or robotic.

As the optimal position for the TMS to achieve suprathreshold stimulation of the target location has been previously computed, the translations and rotations needed to move from the present position to the desired position are computed. If the TMS is held by a passive armature, movement is executed manually, with the readout of the coordinates of the armature as feedback. If the TMS is held by a robot, movement is executed automatically, after a safe pathway (avoiding contact with the subject or other obstacles) has been computed. When properly positioned and oriented, TMS delivery is effected.

The advantages of this method are several. First, placement is extremely precise (±1 mm), much more precise than is possible using hand-held aiming. Second, placement can be computed in advance, rather than by trial-and-error, as is done with hand-held aiming for areas with a measurable behavioral response. Third, once computed, a position can be precisely re-established for subsequent treatments. Fourth, the entire process is mathematically specified and suitable for computer implementation. Fifth, the procedure is suitable for application to any cortical location, not just brain areas in which aiming accuracy can be confirmed by an overt behavioral response. Sixth, once the necessary brain images are acquired, trajectories for stimulating any number of functional areas can be computed.

In an example embodiment, TMS delivery may be effected by means of a robotic arm. Using a robotic arm to move, aim and hold the TMS provides many benefits. First, a robotic arm allows the TMS coil to be placed and oriented with accuracy and precision of—1 mm (location) and—1° (orientation), far exceeding hand-holding. This degree of accuracy and precision is crucial for implementing a high-precision aiming algorithm. Second, a robotic arm allows the TMS to be positioned automatically, i.e., under computer control. Third, a robotic arm allows the TMS to be positioned rapidly, saving time for the patient, experimentor or clinician. Fourth, a robotic arm can accurately re-establish its position on sequential days, which is needed for experiments and treatments applied over a series of sessions. Fifth, a robotic arm allows the TMS to be moved rapidly from one position to another, allowing treatment of more than one location in a single session. Sixth, a robotic arm allows the TMS to be held immobile for long periods of time, which a person cannot practically or comfortably achieve. Seventh, a robotic arm allows TMS to be delivered during PET imaging, without exposing a human holder to radiation.

The present invention is also directed to an inverse design method to produce a desired electric field profile for transcranial/peripheral nerve magnetic stimulation. Such a method may be used to design a variety of coils. Such coils may include multiple winged coils having a concentrated bundle of wires at the center and smooth arcs splayed therefrom at an increasing distance, maintaining the minimum inductance and/or minimum power dissipation possible for a given field profile. Similarly, other coils may be used to produce a spatial gradient across the nerve, maintaining minimum inductance and/or minimum power dissipation.

Coils may be designed in accordance with the teachings of the present invention to incorporate one or more of the following characteristics which aid in the delivery of transcranial magnetic stimulation. In certain embodiments, a coil may be designed to provide for minimum inductance for a given set of field constraints. Further, a coil may be designed to dissipate a minimum amount of power for a given set of field constraints. Similarly, a coil may be designed to provide for minimum inductance and minimum dissipation for a given set of field constraints. In certain embodiments, a coil may be designed with negative turns to reduce the electric field on a patient. Such negative turns also may be provided in a separate layer to similarly reduce electric field on the patient.

BRIEF DESCRIPTION OF THE DRAWINGS

The present invention may be better understood, and its numerous objects, features, and advantages made apparent to those skilled in the art by referencing the accompanying drawings.

The use of the same reference symbols in different drawings indicates similar or identical items.

DESCRIPTION OF THE PREFERRED EMBODIMENT(S)

Aiming is the most fundamental, unresolved issue for scientific and medical uses of TMS. TMS is most often "aimed" merely by observing its behavioral effects. For example, primary motor cortex is frequently identified by adjusting coil position/orientation to achieve a contraction of the desired muscle (e.g., abductor pollicis brevis) at the lowest stimulus voltage. Very recently, image-guided aiming has been introduced (below). Even when image-guided, coil orientation relative to brain anatomy has either been ignored (Paus et al., 1997) or empirically derived (Krings et al., 1997), but it is not based upon a general theory of aiming. Preliminary conjectures as to the mode of interaction between TMS and the brain have been put forward, and emphasize interactions with fibers running parallel to the cortical surface (i.e., horizontal relative to the vertical orientation of the cortical columns). While many accept the horizontal-fiber hypothesis discussed (below), no thorough treatment of its implications for TMS aiming exists. In fact, its predictions do not agree with a growing number of observations. The status and shortcomings of TMS aiming theory and practice are synopsized here, as further background to the present invention.

Figure 2:
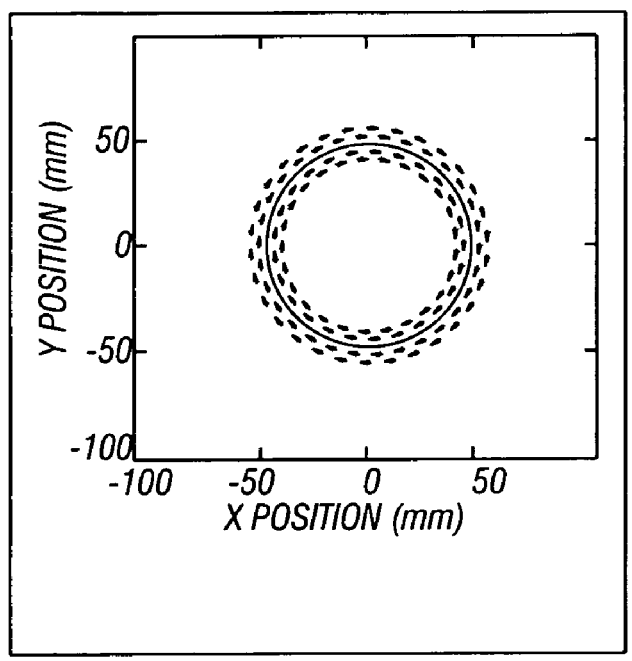
FIG. 2 is a diagram of a typical current configuration for an O-shaped coil.
Figure 3:
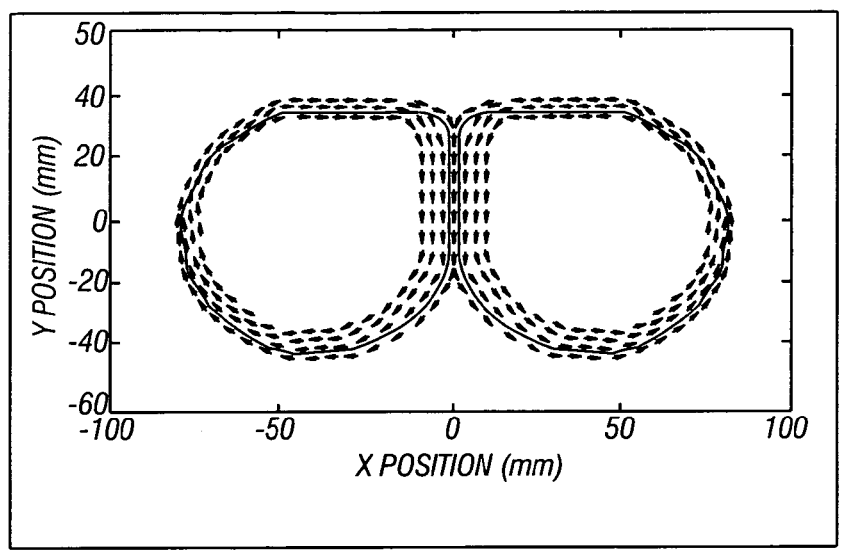
FIG. 3 is a diagram of a typical current configuration for a B-shaped coil.

In a planar electromagnetic coil, the induced E-field parallels the current in the coil, is maximum in the plane of the coil and falls off rapidly with distance from the surface of the coil. Presently known TMS coils are made in two basic geometries: (1) circular (O-shaped, as shown in FIG. 2); and (2) double ring (B-shaped, as shown in FIG. 3). In air, a circular coil induces a circular E-field. Because the current density is evenly distributed around the coil, the E-field is curved and maximum at the edge of the coil rather than at the center. This lack of a focal linear "sweet spot" makes a circular coil very difficult to aim.

A much more focal E-field can be created by placing two circular coils, current flowing in opposite directions (i.e., clockwise and anti-clockwise), next to each other, creating a B-shaped coil. For this coil, the E-field is enhanced where the coils are near each other, because the electric fields from each coil sum. The result is a focal E-field in the center of the coil, oriented parallel to the central region (short-axis) of the B-shaped coil (FIG. 3). The strong, focal E-field makes the B-shaped coil much easier to aim and much more likely to induce a focal brain activation (Roth et al., 1991).

Early O-coil studies (Barker et al., 1985; Barker et al., 1987) observed that motor responses could be obtained from either hemisphere by reversing the direction of current flow. They concluded that this was due preferential sensitivity of neurons to orthodromic currents, recognizing that neural structures "are more likely to be stimulated if they are oriented parallel to the electrical field lines" (Barker et al., 1987). Nevertheless, early researchers remained agnostic on the brain location (cortical vs. subcortical; sulcal vs. gyral) and specific neural elements being stimulated. For example, Yeomans (1990) comments that "localization and orientation effects of magnetic stimulation have not been explained neurally" (pg. 141). In a similar vein, Roth et al. (1991) concludes: "Although the use of magnetic stimulation is growing rapidly, the technique has been applied without a complete theoretical understanding of the induced electric field distribution"; and, "none of these studies define a definitive relationship between the electric field distribution in the motor cortex and the resulting transmembrane potential induced in the cortical neurons."

To this day, many remain agnostic on this matter. As a consequence, TMS position (placement and orientation) follows no coherent theory. Some users position the TMS coil by behavioral optimization (e.g., minimum-threshold muscle twitch); some position carefully, but ignore orientation, using the B-nose convention (discussed below); some orient by reference to prior behavioral-optimization studies; none use an aiming theory.

Day (et al. 1989) were the first to postulate a specific site/mechanism of action for TMS. In the context of a study of primary motor cortex, Day reasoned that "stimuli are likely to activate those neurons nearest the stimulating electrode, that is, those on the convexity of the precentral gyrus". Day knew that an O-shaped coil, positioned flat against the scalp, produced a circular E-field tangent to the gyral crown and at a 90° angle (horizontal) to the (vertical) columnar organization of the cortex at the gyral crown. Day accepted the long-established principle that "a voltage gradient parallel to the long axis of the neuron is the most favorable" (Day et al., 1989). Consequently, Day postulated that horizontal fibers (interneurons, pyramidal tract axon collaterals and afferent axons from cortical and subcortical sites) at the gyral crown must be the directly activated neural elements, with pyramidal neurons (projecting to the spinal cord) being secondarily activated. Note that Day's inferences were based on the assumption that TMS would only be able to activate the brain region nearest to the coil surface, i.e., the gyrus. However, the data of Fox (et al., 1997), Paus (et al. 1997) and the EXEMPLARY STUDY below using PET imaging to detect TMS effects on the brain, clearly indicate that TMS applied with a B-shaped coil preferentially stimulates sulci, rather than gyri. Thus, the premise of Day's reasoning was incorrect.

Experimental support for the horizontal-fiber hypothesis is notably lacking. Day presented no experimental evidence of horizontal fiber activation. The cortical electrical stimulation literature (which excites cortex by passing applying electric potentials directly to the scalp) has consistently utilized current applied perpendicular to the cortical surface at gyral crown (i.e, in the orientation prescribed by the CCCAP) and never horizontally, as would be predicted by Day's horizontal-fiber hypothesis. In fact, no evidence has ever been provided that horizontal-fiber activation results in pyramidal neuron activation or, more importantly for the present proposal, in columnar excitation comparable to that of physiological activation or vertical electrical cortical stimulation.

Theoretical flaws in the horizontal-fiber hypothesis are readily identified. The horizontal-fiber hypothesis postulates that pyramidal motor neurons, located on the anterior bank of the central sulcus, are activated by means of horizontal fibers on the crown of the pre-central gyrus. This is a distance of 0.5–2.0 centimeters. Yet, horizontal fibers extend only 1–2 mm (Jones and Wise, 1978; Jones, 1981). Further, horizontal fibers are isotropic, extending uniformly in all directions within a plane parallel to the cortical surface. The isotropism (lack of a preferred orientation) of the horizontal fibers should translate into a lack of a preferred orientation for TMS, as the E-field should excite a roughly equal fraction of the total horizontal-fiber population in any orientation. This has been clearly disproven by some of the very studies which espouse the horizontal-fiber hypothesis. Finally, the horizontal fiber hypothesis is weakened by the fact that the predominant horizontal element providing for horizontal interactions is the basket cell, which "should be considered a class of large inhibitory interneuron" (Jones, 1981). Thus, the hypothesis that TMS excites pyramidal cells by means of horizontal fibers is quite unlikely.

Figure 1:
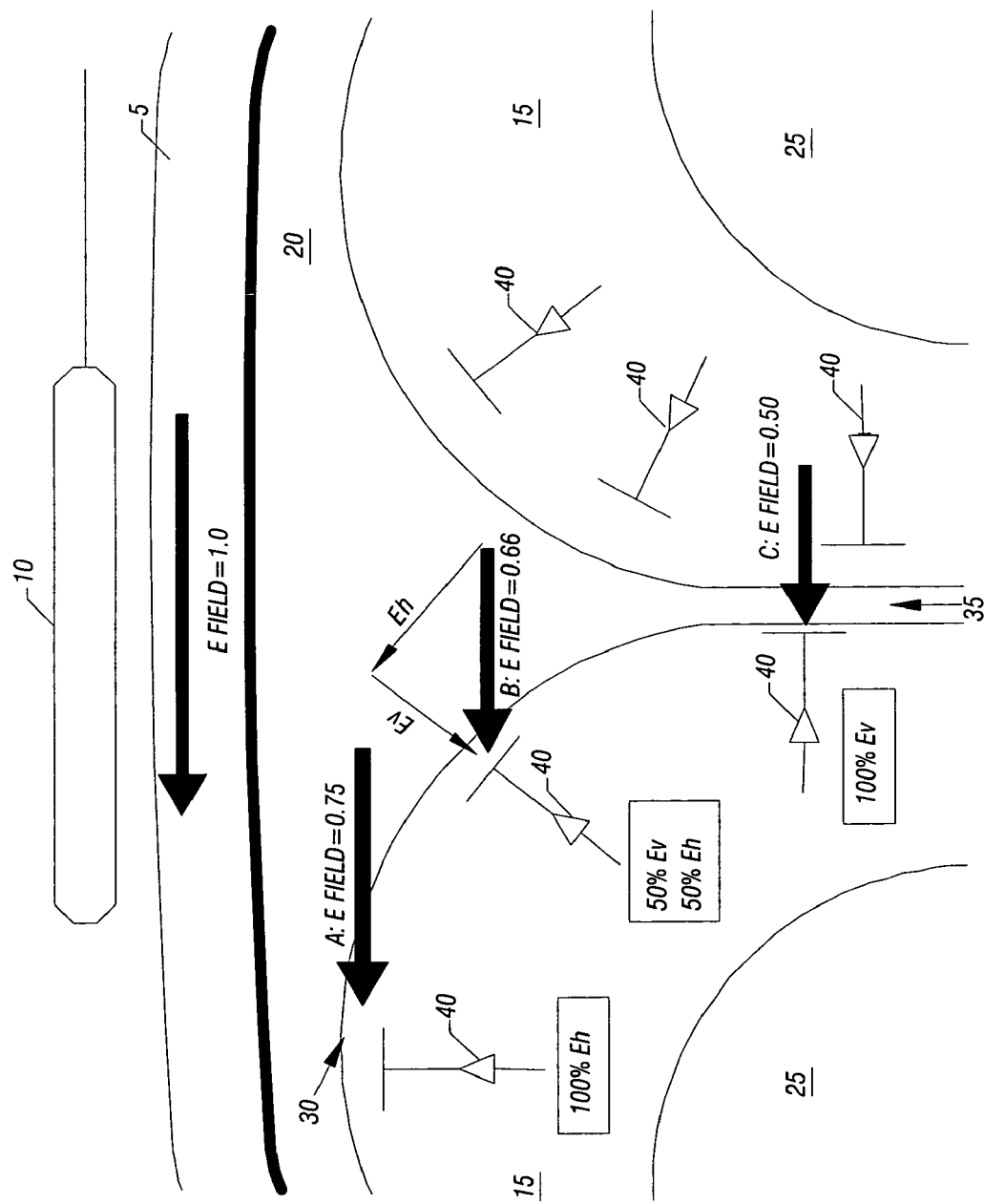
FIG. 1 is a cross sectional diagram of a subject's brain and a B-shaped TMS stimulator positioned thereabove having an induced electric field parallel to the short axis of the coil.

Current common practice is to place a B-shaped coil flat against the scalp approximately over the area to be stimulated, as shown in FIG. 1. Coil orientation is stereotyped, taking no account of the potential interactions between cortical geometry and E-field orientation. Specifically, the TMS coil is customarily positioned such that the short-axis of the coil (flat side of the B) faces the nose and the handle of the coil (round side of the B) faces the occiput: the so-called "B-nose" position. The logic of this orientation convention is not stated in the literature. It may well originate from the physical convenience of standing behind the subject with the coil handle facing the experimenter and the cable draped over the experimenter's shoulder.

Hand-held, non-image-guided application of TMS is the norm. This rather casual approach to stimulation position and orientation likely has several contributing factors. First, hand-held aiming is simple to implement and inexpensive. Second, many users of TMS conceive its effects to be rather diffuse. Consequently, they see little need to be highly precise in aiming. Direct evidence that TMS' effects are highly localized only appeared recently, by PET imaging during TMS (Paus et al., 1997; Fox et al., 1997). Third, no general aiming principle had been enunciated to drive greater precision. Fourth, no systems for facilitating precise, image-guided aiming are available.

Paus (et al. 1997) used a modified commercially available passive digitizing arm, namely a VIEWING WAND® (ISG Technologies, Toronto, Canada) to perform a first-generation form of image-guided TMS. TMS was delivered to the average location of the frontal eye fields (FEF), defined stereotactically (i.e., in standardized coordinates) as the mean of eight, previously published group-mean, PET-activation studies (Paus et al., 1996). Cortical surface geometry (sulcal/gyral location and orientation) was not taken into consideration either for placement or for orientation. Orientation was "B-nose". Anatomical MRI was obtained but was used solely to establish the inverse transformation from the standardized space (Talairach and Tournoux, 1988) to the individual's native image space. No functional markers (e.g., PET during eye movements) were obtained in the subjects either prior to or during the TMS study. The response location was imaged with PET, but was not interpreted relative to group or individual cortical geometry nor was any discussion of an aiming theory included.

Krings (et al. 1997) used a modified SURGICAL ARM® (Radionics, Burlington, Mass.) to stimulate primary motor cortex. The purpose of this study was to compare response locations for TMS and EBS, validating TMS for pre-operative mapping of motor cortex. Position was adjusted to achieve a consistent motor response (thumb twitch). Orientation was based on anatomical MRI, positioning a B-shaped coil with the short axis perpendicular to the central sulcus, in keeping with the recommendations of Brasil-Neto et al. (1992) and Mills et al. (1992). However, Krings offers no aiming theory. The orientation rules which Krings cites (Brasil-Neto et al., 1992; Mills et al., 1992) are specific to primary motor cortex and do not constitute a generalized aiming theory.

Extremely important factors for any TMS aiming system to address are alterations of the induced fields by the stimulation apparatus or the stimulated object. The TMS-induced B field falls off rapidly with the distance from the coil. The induced B field can be altered by nearby ferromagnetic materials, via the creation of secondarily induced B-fields. The magnitude of a secondarily induced B field is a function of the $\mu$ of the metal and the amount of metal; the shape of the secondarily induced B-field is a function of the shape of the object. The secondary B field and the TMS B field will sum, which can distort the net B field in a complex manner. Materials with high $\mu$ are metals. Thus, it is desirable to use a robotic arm having low $\mu$. Furthermore, interaction between coil and arm may be minimized by creating distance between the TMS coil and arm. Biological tissues, in general, are paramagnetic, having very small $\mu$; thus, they do not significantly distort the TMS-induced B field.

Unlike the B field, the brain's TMS-induced E field is subject to alterations from biological tissues, as follows.

Following the TMS-induced E field, currents flow. At the interfaces of tissues whose conductivities differ, charge accumulates. For the head there are three important conductivity interfaces: 1) air and scalp; 2) scalp and skull (outer table); and 3) skull (inner table) and brain. While minor conductivity differences do exist among the several extracranial tissues (dermis, subdermal fat, galea) and intracranial tissues (i.e., meninges, blood vessels, grey matter, white matter and CSF), these differences are small relative to the three major interfaces above. Soft tissues (scalp and brain) are weak conductors; air and skull are non-conductors (insulators). Charge build up occurs, therefore, at the air-scalp, scalp-skull, and skull-brain boundaries. The shape of the head and skull determines the geometry of the charge build up and, thereby, the precise geometry of the E-field distortion. The greatest change in the TMS-induced E field will occur nearest the accumulated charge. Research continues in this area.

The CAPs predict the results of the two orientation-optimization experiments in the TMS literature (Brasil-Neto et al., 1992; Mills et al., 1992), and the two PET/TMS papers published to date (Paus et al., 1997; Fox et al., 1997), and an exemplary study testing the aiming principles.

Figure 4:
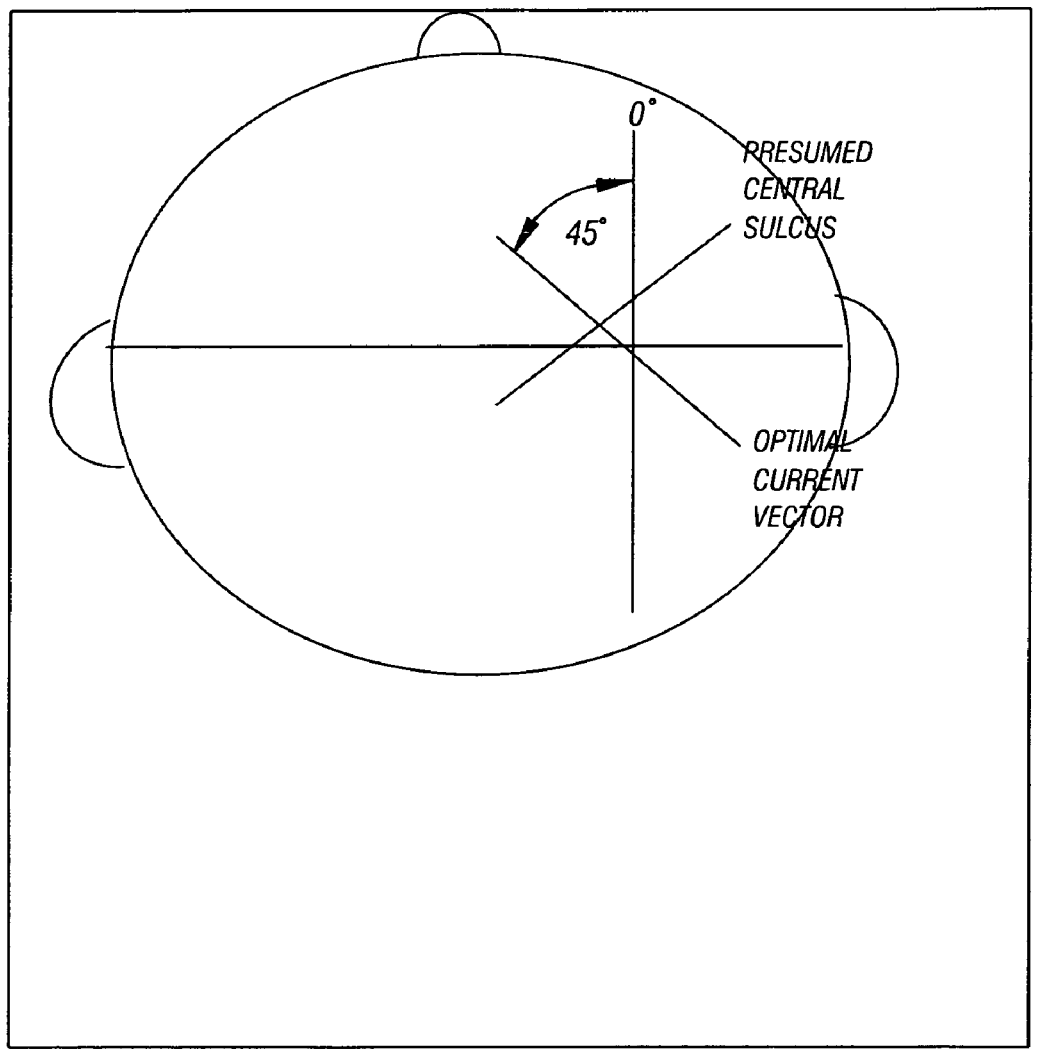
FIG. 4 is a simplified top view of TMS coil orientations used in a prior art study of primary motor cortex.
Figure 5:
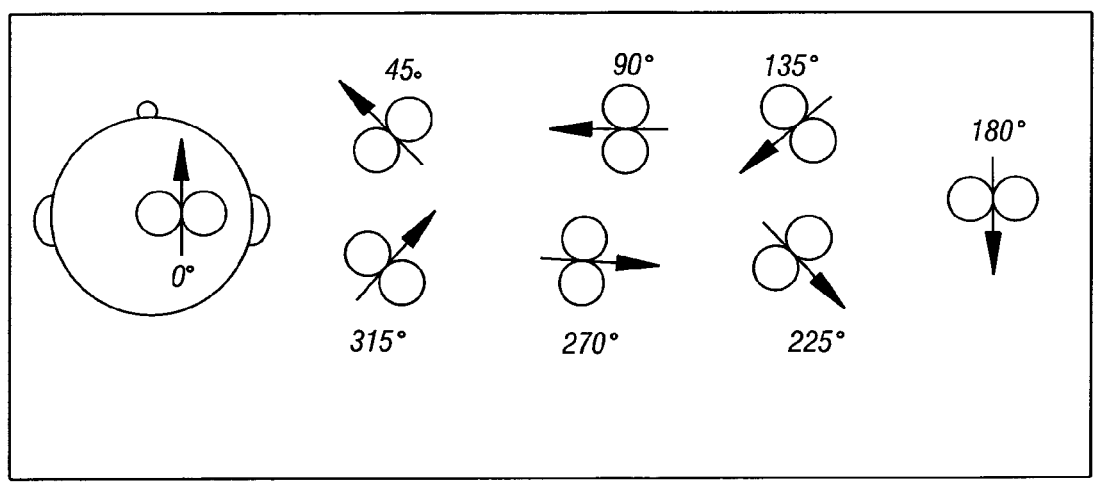
FIG. 5 is a simplified top view of TMS coil orientations used in a prior art study.

The optimal orientation for TMS excitation of primary motor cortex for hand (M1-hand) was simultaneously reported by two independent research teams (Mills et al., 1992; Brasil-Neto et al., 1992). Mills stimulated the left hemisphere; Brasil-Neto stimulated the right. Both groups used the "B-nose" orientation as the reference (0°) orientation, rotating the coil in 45° increments. Both groups found the optimal orientation to be rotated medially 45°, and interpreted this as being perpendicular to the central sulcus, as shown in FIG. 4. The orientation of the E-field (optimal current vector) was normal to the cortical surface of the "presumed central sulcus", as predicted by the CCCAP. Prior art, however, has espoused no general aiming principal nor provided an explanation of the observed effect consistent with known physiology or anatomy. Neither group interpreted this in reference to the columnar organization of cortex, with the E field being aligned with the columns of primary motor cortex, on the anterior bank of the central sulcus. Rather, Day's assumption of selective activation of gyral crowns and, therefore, the horizontal-fiber hypothesis was accepted and cited. Mills recognized that isotropically distributed horizontal fibers cannot explain the observed orientation effect and postulated that horizontal fibers might have an in-plane orientation preference at right angles to the central sulcus. In effect, he postulated a cortical "row" system composed of horizontal fibers, which has never been demonstrated, either anatomically or physiologically.

Brasil-Neto (1992), on the other hand, postulated that "horizontal interneurons which are aligned perpendicular to the central sulcus are preferentially activated by magnetic stimuli", but provided no rationale or supporting data. Both Mills and Brasil-Neto cited studies which indicate the existence of horizontal fibers and that some fraction of these fibers are in the appropriate plane. Neither presented a rationale for preferential orientation (i.e., non-isotropism) of horizontal fibers nor a rationale for their selective orientation perpendicular to the central sulcus. Finally, neither Mills nor Brasil-Neto addressed the great distance (1–2 cm) between the presumed site of stimulation (gyral crown) and the location of human motor cortex (anterior bank of central sulcus) nor the inhibitory nature of horizontal interneurons. Thus, both studies are problematic for the horizontal-fiber hypothesis, even though both cited the horizontal-fiber hypothesis as their underlying theoretical construct.

On the other hand, these orientation-effect results are exactly predicted by aiming principles 2 and 3, which predict maximal activation when the E-field is perpendicular to the cortex and a graded response proportionate to the total Ev. When a B-shaped coil is positioned over a sulcus, the vertical component (Ev) of E is maximal when E is perpendicular to the sulcus, as shown in FIG. 1. This was observed by both orientation studies (Mills et al, 1992; Brasil-Neto et al., 1992), as shown in FIG. 4.

The TMS/PET experiments of Paus (et al., 1997) and Fox (et al., 1997) provide strong evidence for the columnar aiming principles set forth above. Paus applied TMS with a B-shaped coil to the mean location of the frontal eye fields (FEF). The resulting activation was recorded as an increase in cerebral blood flow using $H_2^{15}O$ PET. For purposes of the aiming principles, Paus' most notable finding was that the induced activation was sulcal (not gyral), lying approximately 3 cm deep to the gyral crown. This is in agreement with the prediction of principle 2 and contradicts the prediction of the horizontal fiber hypothesis.

Fox and colleagues applied TMS with a B-shaped coil to primary motor cortex. The coil was positioned and oriented behaviorally, to elicit a contraction of the abductor pollicis brevis at the lowest possible threshold. The resulting activation was recorded as an increase in cerebral blood flow using $H_2^{15}O$ PET. Data underwent a group-mean analysis to create z-score activation images overlaid on the averaged MRI. Again, the induced activation (at the site of TMS application) was sulcal, lying 2–3 cm deep to the gyral crown. Here, the activation site was the anterior bank of the central sulcus, in agreement with known physiology and histology and clearly supporting principle 2.

EXEMPLARY STUDY

The inventors have carried out two studies of aiming principles 2 and 3: one studying E-field intensity (Experiment 1) and a second studying E-field orientation (Experiment 2), as follows:

Experiment 1: By Principle 3, maintaining the E-field at a field orientation but varying the strength of the field should vary the degree of TMS-induced neuronal activity. Eight normal volunteers were imaged by PET while undergoing 3-Hz TMS stimulations across a range of intensities. Stimulation was applied to the Supplementary Motor Area on the medial surface of the right frontal lobe of the cerebral hemisphere. The E-field was oriented perpendicular to the cortical surface, which was also perpendicular to the mid-sagittal plane and exactly 90° rotated from the orientation required by the "B-nose" principle, described above. This stimulation produced strong activation on the medial-bank cortical surface at the location in which the E-field was most perpendicular to the cortical surface, as predicted by Principles 2 and 3. Response magnitude was highly correlated with TMS E-field strength, as predicted by Principle 3.

Figure 6:
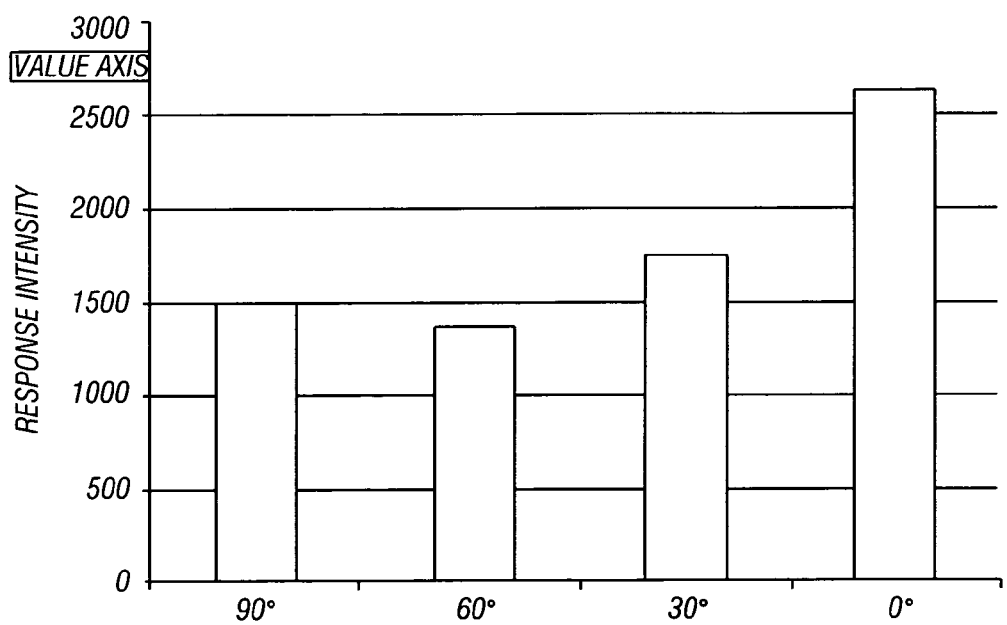
FIG. 6 is a graph of the results of delivering TMS during PET applied to the foot area of primary motor cortex at 0° (perpendicular to cortex), 30°, 60°, and 90° (parallel to cortex).

Experiment 2: By Principles 2 and 3, varying the orientation of the TMS E-field relative to the cerebral cortical surface should modulate response magnitude, with the greatest response being observed when the E-field is perpendicular to the cortical surface. Twelve normal volunteers were imaged by PET while undergoing 3 Hz TMS at fixed intensity but varying orientation: 0°, 30°, 60° and 90° relative to the cortical surface. Stimulation was applied to the foot area of primary motor cortex. As predicted by Principles 2 and 3, the response was located on the bank of the central sulcus, rather than on the gyral crown. Also as predicted by the same principles, response magnitude was highly correlated with TMS E-field orientation, with the greatest response occurring when the field was at 90° to the cortical surface, as shown in FIG. 6.

To take advantage of the aiming principles set forth herein, it is desirable to use a TMS stimulator having properties which allow it to generate an E field having a maximum at a clearly defined location, said location being easily placed in close alignment with a subject's head, so that the E field is directed substantially parallel to the cortical column of interest. Furthermore, in an example embodiment, such a stimulator (or a standard TMS stimulator) may be used in connection with a robotic system to permit for accurate delivery of the E field. It is to be understood, however, that the aiming principles set forth herein may be used in connection with known TMS delivery modes, and likewise, the novel stimulator and delivery system may be used in TMS delivery modes without use of the aiming principles set forth herein.

A flat, B-shaped coil, such as is most commonly used for TMS, creates an E-field that is oriented tangential to the scalp surface upon which it is placed. By Aiming Principles 2 and 3, this E-field configuration is optimal for stimulating the banks of sulci in which the sulcus is oriented perpendicular to the scalp surface (e.g., in FIG. 1). The same principles, however, predict that this E-field configuration will be unable to stimulate the cortical surfaces parallel to the scalp, i.e., the gyral crowns. The gyral crowns compose approximately 30% of the total cortical surface. Thus, there is a need for a TMS coil capable of stimulating gyral crowns. By Principles 2 and 3, this would require an E-field oriented perpendicular to the gyral crown, i.e., essentially perpendicular to the scalp surface.

Figure 7:
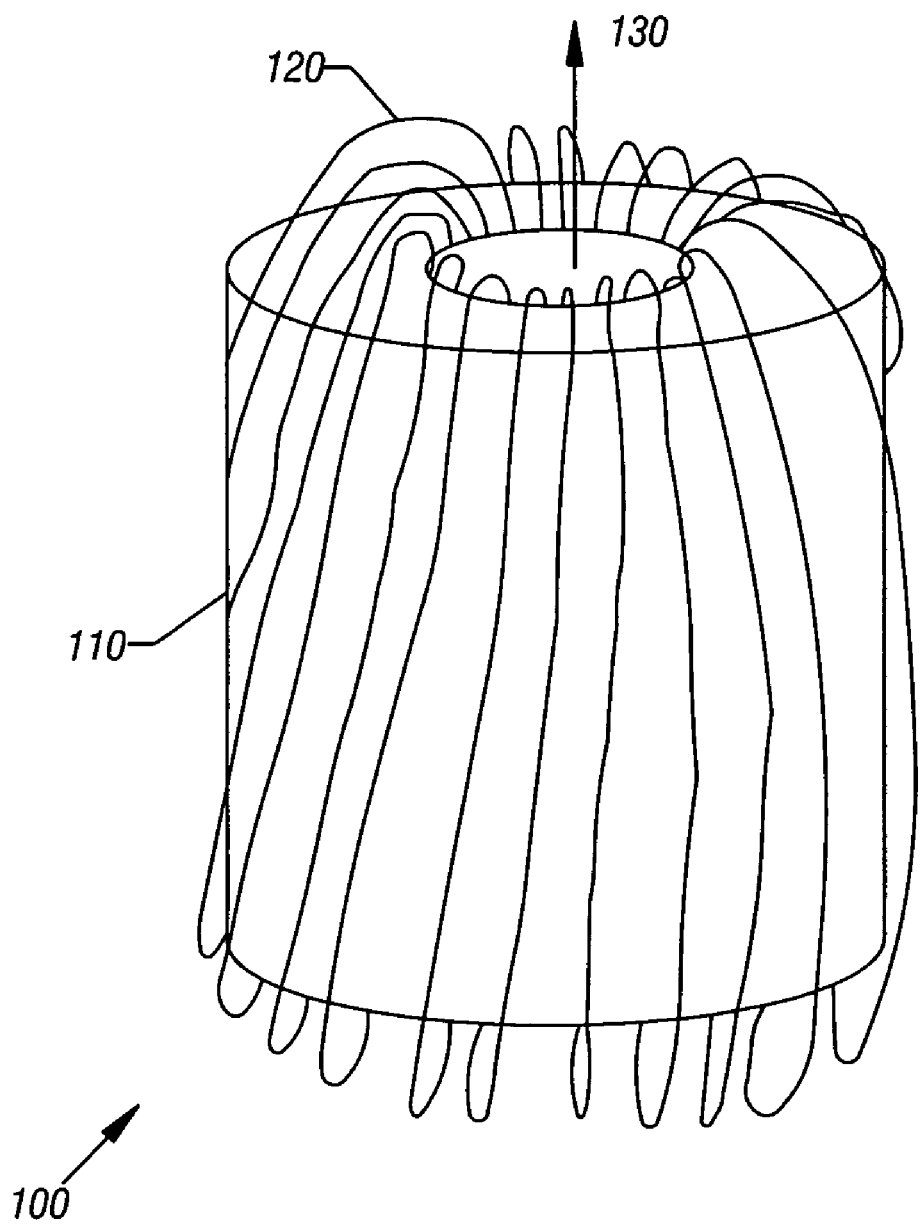
FIG. 7 is an isometric view of an example TMS stimulator according to the present invention.

FIG. 7 is an example embodiment of a TMS stimulator capable of stimulating gyral crowns, according to present invention. As shown in FIG. 7, TMS stimulator 100 includes a body portion 110 and a coil portion 120. In an example embodiment, the body portion 110 may be made of air, ferrite or other materials with $\mu > 1$. Stimulator 100 may be surrounded by a conducting fluid. The conducting fluid can fill the central portion of the coil portion 120. The conducting fluid can fill the space between the coil and targeted body tissue. The purpose of the conducting fluid is to provide efficient induction of the E field produced by stimulator 100 through the tissue surface, directed according to the coil design. In certain embodiments it may be desired to construct the body portion 110 of a non-conducting material and include an insert through at least a portion of the hollow portion of the cylinder which may be made of a ferromagnetic material such as iron. The coil portion 120 may be made of wire, such as copper or the like. Via conductors (not shown in FIG. 7), the coil portion 120 is connected to a power supply. The power supply is used to provide a current through the coil, which generates an electric field emanating from the stimulator.

In an example embodiment, the power supply may include a high energy capacitor bank, which when discharged provides a high current through the coil portion 120. In an example embodiment, the electrical current may be relatively strong (between about 1000 and 2000 amps) and last for a relatively short period of time (between 50 and 250 microseconds). To deliver such a high intensity, short pulse current, the power supply may include a capacitor bank having a very high storage capacity on the order of 50 microfarads charged to a potential of 2000–6000 volts. Preferably, the capacitor bank is made of high duty material to withstand the current generated. For example, the capacitor have a capacitance of 50 MFD and a voltage rating of 7.5 kV may be made physically larger to extend the lifetime from an estimated $10^5$ pulses to $10^8$ pulses. Furthermore, in an exemplary embodiment, the power supply, conductors, and the TMS stimulator may be water-cooled to reduce operating temperature.

Although shown in FIG. 7 as a cylinder, it is to be understood that body portion 110 may be various shapes, such as cone shaped, cylindrical, ellipsoidal, rectangular, and the like. Further, as shown in FIG. 7, the coil portion 120 is preferably toroidal shaped, however, it is to be understood that the coil may be constructed in various shapes.

In an example embodiment, the body portion 110 may comprise a cylinder having a diameter between about 10 and 20 centimeters, and a hollow core having a diameter between about 0.5 and 2.0 centimeters.

In an example embodiment, the wire portion 120 extends substantially around the body portion 110 in a toroidal shape. In certain embodiments, the wire used may have a diameter between about 0.1 and 1.0 millimeters.

By use of such a design, when energized by an electric current, the TMS stimulator 100 generates a maximum induced electric field extending along the long axis 130 of the body portion 110.

In an example embodiment, TMS delivery may be effected via use of a robot. More specifically, a robot having six or more degrees of freedom may be used to appropriately position and orient the TMS coil in a precise location and orientation for most effective delivery of induced electric field. Without a sixth degree of freedom, the orientation aspect of the CCCAP described above cannot be implemented. In an example embodiment, a surgical robot having five joints may be modified to add a device to hold the TMS stimulator and provide for a sixth degree of freedom. Alternately, a robot having six degrees of freedom may be used.

The robot may be a medical robot to provide benefits of a robot safe and effective for use with human patients. Such a robot may be controlled by a computing system, such as a PC. Robot tool motion and orientation may be controlled from appropriate software programs. Such programs may include control for robot arm position monitoring, position modeling, plan movement modeling, and movement model execution. Additionally, sensors may be provided so that XYZ position and angles for each of the joints of the robot arm may be obtained in real time. Motion commands may be executed in a coordinate system native to the robot. In an example embodiment, the robot arm may be moved from point to point in a smooth manner using a 3-D mouse, SPACE MOUSE™, or keyboard input. By use of such a robot, maintenance of a pre-specified treatment position may be more precise and accurate than a passive arm or a hand-held device. Furthermore, a robot allows movement through a treatment zone (rather than treatment of a point) and further allows precisely timed treatments of multiple sites in a single session.

Via use of such a robot, TMS may be effective for use in connection with pre-operative mapping, inter-operative monitoring, and treatment of conditions, such as long-term depression, and for clinical activity and functional mapping using TMS and PET. Additionally, by use of a robot, a means is provided to export a generic treatment plan. In other words, a coordinate system may be developed and standardized across different patients, labs, and the like. Furthermore, such use of a robot is particularly useful with regard to a treatment program in which a patient is subjected to TMS over a repeated number of days.

Figure 8:
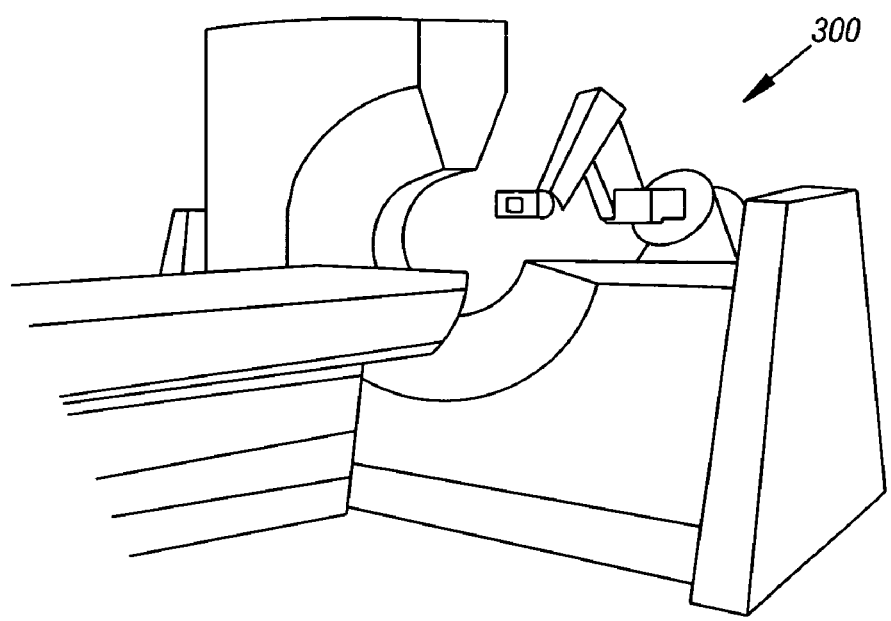
FIG. 8 is a diagram of a TMS attached to a robot and placed behind a PET scanner, to acquire a PET functional imaging study during TMS stimulation. The upper right quadrant of the PET is shown in a cut-away view, to allow the robotic TMS system to be illustrated.

In an example embodiment, a NEUROMATE™ stereotactic assistant system (ISSI, Sacramento, Calif.) was modified for use. FIG. 8 shows an overview diagram of the NEUROMATE™ system 300 as used in connection with PET imaging. The exemplary surgical NEUROMATE™ robotic arm was modified to convert it from a system for frame-based, intra-operative probe positioning into a system for frameless, extra-operative, positioning and orientation of an induced E-field.

Robotic devices must be used with caution in the presence of persons. In an example embodiment, a robot such as the NEUROMATE™ specifically designed for use by and with humans is desired. Benefits include that it moves slowly, such that it can easily be stopped prior to any collision, loss of electrical power renders it immobile in its current position, i.e., it does not return to a "parking" position or make any sudden motions. Further, such a robot may require a key and a recessed button to actuate, being used only under direct supervision.

A TMS-coil holder was constructed for the TMS coil to adapt to the NEUROMATE™. In the example embodiment, the TMS tool-holder included a tool-rotation axis, as lacking this, changing coil orientation would require establishing a new arm posture, with only a very limited number of orientation angles (at a given location) being possible. In addition, the tool holder serves as a stand-off, creating a distance between the final limb of the robotic arm and the TMS coil. This distance decreases effects of the metal arm on the coil's B and E-fields. In addition, this helps keep the metal arm out of the PET field-of-view, thereby lowering the possibility of PET-image attenuation artifacts. Finally, the tool holder permits orientation sensing and motorized, computer-controlled coil-orienting. It is to be understood, however, that a tool holder need not include a TMS-rotation axis, and that in other embodiments (such as a 6-joint robot), the TMS coil may be adapted directly to a robotic arm.

Figure 9:
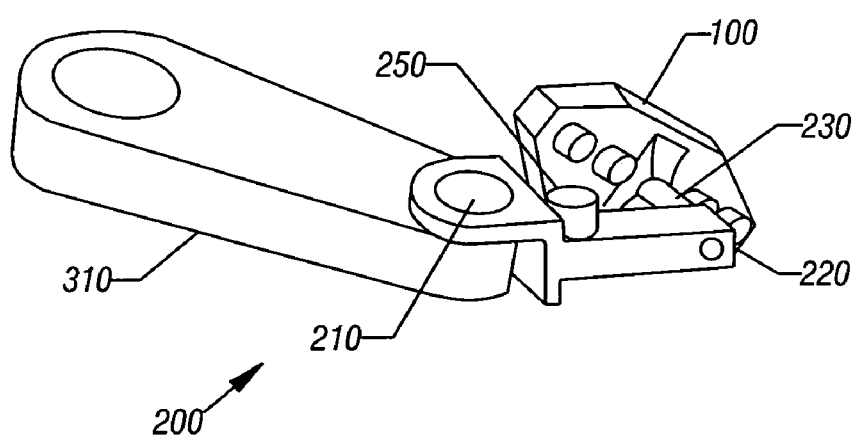
FIG. 9 is an isometric view of a TMS tool holder according to the present invention.

In the example embodiment, the TMS-coil tool holder was constructed of fiberglass. However, in other embodiments, the tool-holder may be made from a number of other materials, such as acrylic, fiberglass, delrin, or the like. As shown in FIG. 9, the tool holder 200 includes a proximal end 210, which may be machined to interface with the robotic arm tool-mounting plate 310. The distal end 220 of the holder may have a rod 230 mounted to the TMS coil 100 and allow rotation about the coil's z-axis. For the example embodiment, the robotic arm tool mounting plate 310 comprises the fourth and fifth axes of the robot, and the tool holder 200 comprises the sixth degree of freedom. In an example embodiment, the body of the holder 200 is approximately 8" and houses a plastic belt turning a more proximally placed rod to mechanically link the orientation of the rod 230 and the TMS to the orientation sensor 250.

In an example embodiment, a precision rotional sensor 250 may be mounted on the end of the proximal (belt-driven) rod. In an example embodiment, the sensor may be a single turn (340°, 10 kΩ) precision resistive potentiometer with +/−1% linear rating. The output of the sensor specifies the orientation of the TMS coil. The sensor's output may be conveyed to TMS delivery software via tool-sensing electrical contacts on the robotic arm tool-mounting plate 310. In neurosurgical applications, these contacts are used to monitor the depth of tool (e.g., drill-bit or wire electrode) passed through a stationary tool holder. In the present application, they may be used to monitor orientation rather than depth. Additionally, a stepping motor may be added, allowing active rotations of the TMS coil.

As discussed above, the NEUROMATE™ was designed as a system for framed stereotaxy. A patient is registered to the NEUROMATE™ by having his (or her) head placed within a metal ring that is rigidly mounted to the NEUROMATE™ by means of a pedestal attached to a long leg, which forms the base/stand of the NEUROMATE™. For TMS delivery, the robotic arm was converted into a frameless stereotactic system, capable of being rapidly registered to a subject in any position within the operating range of the robot arm, including supine in the PET scanner. It is to be understood, however, that the methods and apparatus of the present invention may be used in conjunction with framed stereotaxy.

In an example embodiment, this registration process may use a manual digitizer to collect points from the subject's scalp, which may be registered to the scalp surface modeled from that subject's image, such as obtained from MRI. In other embodiments, the robot may be used in an interactive mode to collect these scalp points.

In an example embodiment, a 5-axis manual digitizer (Microscribe 3D) may be permanently mounted to the robot chassis for use as required. The positional relationship between the digitizer and the TMS probe may be calibrated and thereafter should remain constant, although it is recommended that calibration be verified for each use of the system.

Typical surgical robotic devices come equipped with a stand designed for framed stereotaxy. This stand has a long foot which prevents it from being placed sufficiently close to the PET for use during TMS/PET. Thus, a shallow, wide, weighted, four-wheeled, cart may be used having weight and width to prevent tipping. Preferably, the wheels are retractable, to allow the system to be completely stable when in operation, yet re-positionable to optimize placement of the robotic arm relative to the PET.

As presented above, passive digitizing arms can be used for image-guided TMS-delivery. Both Paus (et al., 1997) and Krings (et al., 1997) used commercially available passive arms designed for frameless stereotaxy to assist with TMS aiming. However, these two systems suffer from significant and virtually identical limitations. Neither can be fixed rigidly in position; that is, both are manual digitizers but neither is a holding device. (Paus mounted the TMS coil to a separate, home-made holding arm; Krings held the TMS coil by hand.) Neither system can digitize or visualize tool orientation, as both are five-joint arms with no capability for rotation about a tool axis. (Paus fixed the coil in the B-nose orientation; Krings hand-held the coil in the orientation recommended by Brasil-Neto [et al., 1992] and Mills [et al., 1992]). Not unexpectedly, neither tool has software for visualizing tool position/orientation vectors. Neither system has any capabilities for modeling the E-field, visualizing E-field lines relative to brain anatomy. Finally, neither system is robotic.

An active (robotic) arm has clear long-term advantages. Ideally, treatment positions are pre-specified, with the arm moving to and maintaining the treatment position. A robotic system can carry out this function more precisely and more accurately than a passive arm. Further, only a robotic system readily combines the tool aiming and tool holding functions. Finally, only a robotic arm allows movement through a treatment zone (rather than treating at a point) or allow precisely timed treatments of multiple sites in a single session.

The PET image, the MR image, the manual digitizer, and the robotic arm robot have different coordinate-reference frames. In an example embodiment, a whole-brain, high-resolution (1 mm$^3$), T1-weighted MRI may be used to create a reference space within which all objects become registered. This image format provides ample anatomical detail for precise registration. Additionally, all images may be standardized by removing differences in orientation and position between patients. In an example embodiment, each patient's reference MRI may be rotated and translated (but not scaled) to the alignment of the Talairach and Tournoux (1988) atlas. This six-parameter spatial normalization (of the reference MRI) may be performed using the previously validated SN software (Lancaster, et. al. 1995). This software may be used to freely rotate and translate a 3-D brain image to position it in a standard pose. The standard pose is with the brain's anterior commissure (AC) located at x, y, z,=0,0,0. The line between the anterior and posterior commissures (AC and PC) adjusted to lie along the y-axis and the inter-hemispheric plane fitted to the y-z plane at x=0. The reference MRI may serve as the reference frame for coordinates from: functional images (PET), the head-surface digitizer; the robotic arm, the TMS coil (held by the arm), the standardized head models; and the TMS-induced B and E fields.

In an example embodiment, the robot may be moved in a user-guided visual-feedback mode for manual positioning and holding of the TMS probe. Preferably, the robot may be moved from point to point in a smooth manner using joy stick-like or keyboard input. For example 3-D mouse/joystick, such as a SPACE MOUSE™ may be used in conjunction with a supervisory PC controller to send motion commands to the robot's on-board controller. Motion commands may be executed relative to: (1) the tool coordinate system referenced to the face of the TMS; (2) a reference MRI (aligned but not scaled to the Talairach & Tournoux [1988] brain); and (3) the global coordinate system native to the robot. In order to implement this control feature, the supervisory controller may use a robot inverse transformation to calculate joint coordinates needed to accomplish an incremental change of position relative to tool coordinates. The calculations may take into account arm configuration and joint rotation limits, and will format the commands to the world space required by the supervisory controller.

In an example embodiment, the communication protocol, position-sensing interface specifications, movement sensing interface specifications and complete kinematic equations for the robot arm may be developed using, for example, Microsoft Visual C++ on a Pentium-level PC.

The protocol used by the supervisory control software to communicate with the robot controller may use RS-232 connections and protocol to send instructions and retrieve supervisor-level data from the controller. Using such protocols, a Visual C++ application may support all motion type commands, including an exclusive stop command and polling commands for status.

A second serial port of the PC may be used to get robot arm position data and status. The communication protocol may be similar to that for the supervisory control software discussed above. A multi-port serial I/O board may be added to the PC to support simultaneous access to both ports from the same computer. Supervisory control software routines may be used to read this port and obtain x-y-z position and angles for each of the six joints of the robot arm. Furthermore, forward and inverse kinematic equations may be used to specify and modify arm pose.

In an example embodiment, the patient's head and the robot may be registered to the MR reference frame for each patient and each TMS session, as accurate positioning of the robot forms the basis for registration of the TMS coil relative to the head. Physical coordinates digitized about the surface of the head may be used to register the patient's head and to calibrate the digitizer relative to the MRI reference frame.

As disclosed above, the manual digitizer may be permanently mounted on the robot, enabling direct digitizer-to-robot calibration. Rigid-body coordinate-transformation matrices may be calculated between the robot, the digitizer, and the MR reference frame.

For patient registration, a manual 3-D digitizer (MicroScribe 3DLX) may be used to acquire a "cloud" of distributed points on the patients head in a hat-file format (Pelizzari et al., 1989). An MRI surface (head-file format) with 6000–7000 points uniformly distributed about the head may be extracted from the subject's standardized MR image using, for example, convex hull (CHSN) registration software (Lancaster et al. 1999). A coordinate transformation for calibration (or registration) may be determined by fitting the digitized hat "cloud" (patient) to the detailed head (MRI) surface. The fitting method used may be an iterative least square technique that has been shown to provide excellent results for co-registering PET, CT, and MRI (Lancaster et al., 1997). Patients may be positioned within the PET scanner with head constrained. The CHSN software may be used for fitting the hat to the head surfaces and calculating a head-to-MR transform matrix. The digitizer-to-MR matrix is identical to the head-to-MR matrix, as both are calculated using the manual digitizer and the head surface.

For robot registration, the robot-to-digitizer transform matrix may be calculated using fiducials for which both digitizer and robot coordinates can be readily determined. A pseudoinverse method may be used to calculate the transformation matrix (Castleman, 1996). The robot-to-MR transform matrix may be calculated by concatenating the transform matrices for robot-to-digitizer and digitizer-to-MR.

When the TMS coil is permanently mounted on the robot arm, the TMS-to-robot calibration transform matrix can be calculated. This may be done with the coil in a designated zero-degree orientation relative to the mount. Three parameters (x-y-z position, coil, tool, or z axis orientation, and rotation about coil, tool, or z-axis) are used to fully aim the TMS coil. These may be determined using the manual digitizer to record fiducials on the coil's x- and y-axes. Using these data, equations to calibrate the robot can be determined and robotic coil aiming enabled. This calibration should remain fixed but may be verified periodically. Coil aiming may be extended to the MR reference frame using the robot-to-MR transform matrix. Only position and z-axis orientation are under direct control of the robot. The uncontrolled rotation about the z-axis may be calculated for each robot arm position. Targeted orientations of the coil about its z-axis may be achieved using the manual digitizer and/or the orientation sensor.

In order to overlay PET (functional) and MRI (anatomical) images as part of treatment planning, the PET images may be registered to the MR reference frame for each patient. PET images may be co-registered to standardized MR images using, for example, the convex hull (CHSN) registration software (Lancaster et al., 1999). Convex hull surface is extracted from both MRI and PET images. These models remove concave regions that are well resolved by MRI but poorly resolved by PET. However, the convex brain surface is identical in both imaging modalities and proves and excellent surface for surface matching and, thereby, volume registration. The CHSN software (Lancaster et al., 1999) uses the convex hull of the brain, a simplified surface which is highly similar across imaging modalities, for registration and spatial normalization. An iterative least square method is used to fit the convex hull from PET (hat format) to the subject's reference MRI (head format), allowing only rotations and translations of the hat data (Pelizzari et. al., 1989). This fitting method has very small error: mean RMS errors, measured as distance between the two convex hulls, were reported to be less than 1 mm (Lancaster et al., 1999). A PET-to-MR coordinate transformation matrix may thus be calculated by the CHSN software.

There are four principles that can be used to estimate important aiming parameters of the TMS stimulator without resorting to comprehensive E-field calculations. First, the E field magnitude of figure-8 coil tends to remain strongest at points along the central axis perpendicular to the plane of the coil (z-axis). Second, the E-field magnitude rapidly decreases with increasing distance from the surface of the coil. Third, inside a conductor (e.g. brain) the surface charges reduce the E-field magnitude relative to what its magnitude would be at the same point in air. Four, under certain conditions of symmetry a weak conductor (e.g. the brain) will not change the direction of the E-field on the coil's z-axis. For example, if the coil is placed tangential to the head, at a point of fairly symmetric curvature, this symmetry about the z-axis will tend to cancel distortions that would change the direction of the E-field. These "on-axis" principles, in conjunction with the columnar aiming principles may be used to accurately aim the TMS.

To create a safe and effective treatment plan, the following exemplary steps may be performed. First, a cortical stimulus-delivery site must be selected. Second, at the stimulus-delivery site, the columnar orientation must be determined. Third, TMS coil aiming parameters must be determined. Fourth, a model of the TMS E-field (corrected for head-induced distortions) must be determined. Fifth, models of the TMS coil and patient head surface must be provided for collision avoidance. However, it is to be understood that in other embodiments, more or fewer steps may be performed.

In an example embodiment, these steps may be performed via TMS planning software. Site selection may be done interactively while viewing a high-resolution MR image of the brain in three orthogonal views. The columnar orientation at the treatment site may be determined from the high-resolution MRI by means of cortical-surface extraction, as cortical columns are oriented perpendicular to the cortical surface. Once the treatment site and its columnar orientation are established, the on-axis plan proceeds by determining the TMS coil position for aiming. This may make use of a 3-D front-surface model of the coil and the patient's 3-D head surface model to avoid head contact. The coil position closest to the head in which the on-axis E field parallels the cortical columns at the treatment site may be established. The TMS coil aiming parameters (position, coil z-axis orientation, coil y-axis orientation) may be determined and used to direct the robot to aim the coil during TMS delivery.

Using the TMS coil aiming parameters and the treatment site configuration (location, column orientation), the induced E field may be modeled using on-axis data to predict its magnitude at the delivery site. A fully 3-D approach, including effects of the patient head may be modeled for each subject using EMAS (Ansoft, Pittsburgh, Pa.) and anatomical data derived from CT scans.

In still further embodiments, methods for accelerating calculations of electric fields may be provided. EMAS is a general purpose Maxwell's equations solver. Because of its generality, it is slow and uses a lot of computing resources. Calculation of the electric field for a single coil position may require several hours for interactive, image-guided imaging abbreviation of this computation time is desirable. Computations may be accelerated chiefly by introduction of simplifying assumptions. For example, because the skull is a poor conductor, the magnetic fields produced by induced eddy currents can be safely ignored (Davey et al, 1991). As a consequence, the magnetic field produced by the TMS coil may be modeled as being unaffected by the head. Further, the skull is 100 times less conductive than soft-tissue. Therefore, it may be possible to treat the skull as a perfect insulator; treating all regions outside the skull as air. In addition, when using a standardized head model, it may be possible to pre-compute (and store as look-up tables) the E-field for often-stimulated brain zones, such as M1-hand. The E-fields for an individual could be then be calculated as a perturbation of the pre-computed values. Finally, it is possible that field estimates based just on the local skull curvature may be quite accurate and provide considerable computational savings.

To support safe movement of the coil about the head, 3-D models of the head and TMS coil surfaces may be defined, and a polygonal model of the surface of the TMS coil created. Full-surface polygonal models of each subject's head may be created from the high-resolution 3-D MR image. By thresholding the MR image to the head surface, a mask defining the full 3-D volume of the subjects head can be obtained. Using 3-D morphological dilation, a second volume that is guaranteed to be a minimum distance from the head surface can be created. The dilated head volume may be used to model a volume with a realistic safety margin for use in collision avoidance control when moving from point to point about the head. The undilated model may serve to determine closest approach without contact in final positioning. The surfaces of the head models may be extracted and stored using the marching cubes algorithm and its standard storage format (Schroeder et. al., 1996). Additionally or alternatively, collision avoidance may be provided by the operator (run/stop button with absolute shut-off switch).

In an example embodiment, TMS delivery software may be used to position the TMS coil exactly as prescribed by the planning software. This software may provide accurate robot-controlled positioning of the TMS coil along and about its z-axis. Additionally, movement and pose strategy may ensure safe, effective operation. Finally, feedback to the delivery software may monitor this operation.

In exemplary software, a graphical user interface may be provided, in which the user is prompted for input and presented with options for delivery of TMS. The TMS delivery may proceed and display status information. A graphical user interface may monitor movement of the robot/TMS coil about the patient's head. Polygonal models developed for collision avoidance may be used for rendering 3-D views of the head and TMS coil body. A 3-D polygonal model of the robot with TMS coil mounted may be used to create a real-time 3-D display of the robot moving about the head surface. View orientation may be user-selectable to provide unobstructed viewing of the patient's head. This display feature may be provided as animation during treatment planning to simulate delivery.

For a given TMS coil location and orientation, several arm poses will often be possible. Environmental factors, including TMS coil electrical and cooling lines, PET scanner housing, patient table and head holder, etc., may be accommodated when selecting best pose. Joint configuration may be under control of the supervisor software developed to move the arm, which are computed using the forward and inverse kinematics equations of the robot. The user may be presented with several options and asked to select one for the treatment delivery.

In an example embodiment, the robot can position the TMS coil but cannot rotate it about coil's z-axis, therefore the coil angle may be adjusted manually. Software may use the manual digitizer to measure the TMS coil z-axis rotation angle. In embodiments with a rotational sensor, the sensor may be used for coil-angle sensing, in preference to the manual digitizer. The current and target angle, and the difference may be actively displayed. Manual orientation may be done with TMS housing away from the head at the position where the robot has already aligned the coil along its z-axis. The z-axis rotation angle sensing may be automated using the precision rotary potentiometer. The sensor may be connected to the robot controller via its existing wiring harness. Movement toward the head along this treatment axis may be done after adjusting coil angle.

The cortical column orientation throughout the treatment volume may be determined by a method using both inner and outer cortical surfaces. The first step may be a semi-automated extraction of the cortical surface, using, for example, the MEDx (Version 2.1, Sensor Systems, Inc.) image processing software. This step requires approximately 20 minutes per surface. The extracted surface may be refined using morphologic operators (dilation, erosion, and 3-D connectivity routines), also within MEDx. Both inner and outer cortical surfaces for the treatment volume, including all visible sulci, may be extracted and used to create a binary mask of the cortical columns within the treatment volume. The binary mask may be used to create a set of normal vectors that uniformly fill each voxel within the mask. A 3-D Euclidean Distance Map (EDM) (Russ 1996, Gonzales and Wood 1992) may be used to fill the binary mask with distances from the outer to the inner surface. The EDM may then be smoothed with a 3-D Gaussian filter to produce a smooth gradient of values from the outer to inner cortical surface bounds. A normal vector may then be calculated for each voxel within the binary mask from the gradient of EDM values (Schroeder, et. al. 1996). These normal vectors may be converted to unit normal vectors. The sense of the unit normal vectors may be to point into the brain (orthodromic column direction). This method, based on the EDM provides a smooth and continuous orientation change for the normal vectors. These normal vectors may be used for the orthodromic orientation of the cortical columns for each voxel in the binary mask.

A 3-D scalar map of columnar component of E-field may be accomplished using 3-D models of the E field accounting for the head a set of coil aiming parameters (position, coil z-axis orientation, and coil rotation), and the 3-D model of cortical column orientations. Using the TMS coil's treatment parameters to orient the E-fields relative to the head, the scalar product of E-field vectors and cortical-column unit vectors can be calculated, yielding E-field magnitude along cortical columns (Volts/cm) for each voxel within the treatment volume. The result will be a 3-D scalar map of the columnar component of the E-field throughout the treatment volume. This map may be used to overlay onto the MR image to see the planned treatment. Modeled treatment effects may be visualized as a pseudo-color overlay on the anatomical image. An option may be provided to display the absolute value of the E-field magnitude, and a method to enable/disable the overlays. The user may adjust TMS coil global E-field magnitude and a threshold value for display to see the effect of these on target and non-target cortical regions. Since the E-field scalar map depends on both cortical column and coil orientation, a "jog" feature to interactively reposition the TMS coil may be provided to help the user optimize the magnitude in a targeted region. This jog feature allows small increments of movement along and rotations about the orthogonal tool axes after they have been verified safe (non-interfering with the avoidance volume) by the supervisory controller.

In certain embodiments, the metal in the PET gantry might alter the TMS-induced B and E fields. If so, this effect must be included in the E-field modeling. Conversely, the TMS B-field might affect the performance of the PET photo-multiplier tubes, which may be resolved with μ metal shielding during TMS/PET. Further, the TMS coil and coil holder may excessively, regionally attenuate the emitted annihilation photons. It is to be understood that standard attenuation corrections may suffice to correct for the effect of the TMS coil.

Figure 10:
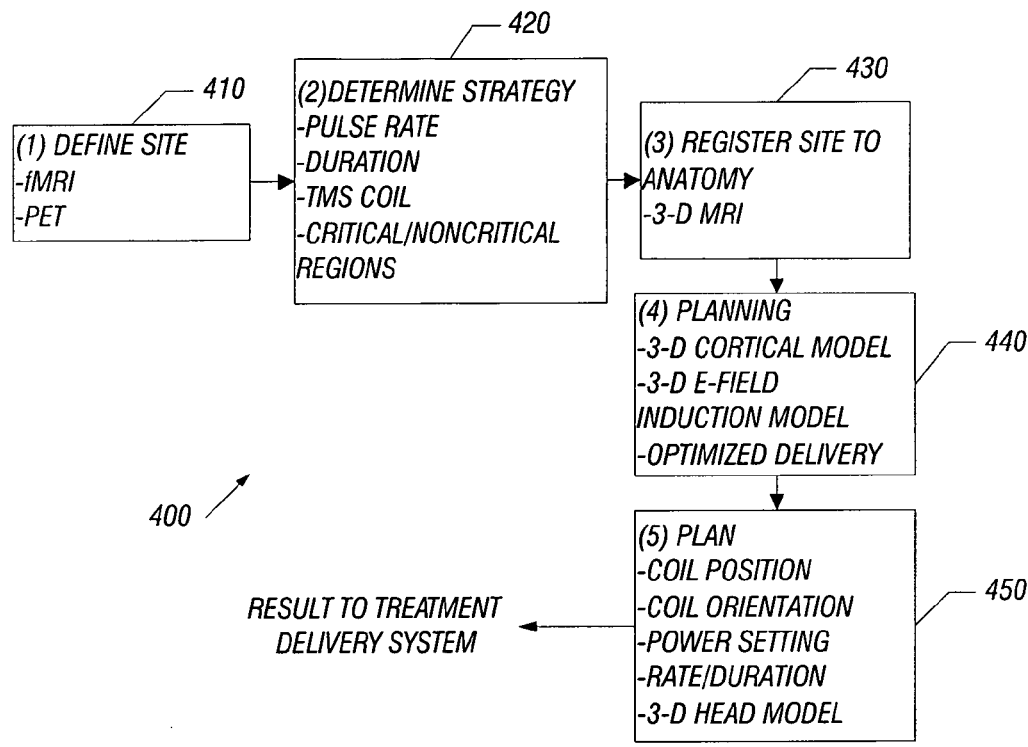
FIG. 10 is a flow diagram of an example TMS treatment planning system according to the present invention.

FIG. 10 is a block diagram of an example TMS treatment planning system according to the present invention. As shown in FIG. 10, in an example treatment planning system 400, a desired site is defined at step 410. For example, the desired site may be defined via various imaging techniques, such as fMRI or PET. Next at step 420, the TMS delivery parameters may be determined. These parameters may include, for example, the desired pulse rate, duration, TMS stimulator design, and a definition of critical/non-critical regions. Cortical regions may include sites to avoid during treatments or regions of known connectivity to targeted regions that might alter the net stimulation to the targeted region. Non-critical regions might be regions known to have little connectivity to the targeted region.

At step 430, the defined site may be registered to the subject's anatomy. In an example embodiment, the registration step may be performed via use of a 3-D MRI. At step 440, planning tasks may be performed. These planning tasks may include modeling various elements in order to optimize TMS delivery. These models may include, for example, a 3-D cortical model of the subject's brain, to determine the accurate location of cortical columns and cortex regions. In addition, a 3-D E-field may be modeled for the chosen TMS stimulator design. Further, in an example embodiment, a 3-D induction model may be performed also. The 3-D induction model is derived from the scalar product of the E-field and the cortical column direction, and is the net volts/cm estimated for cortical columns. Based on all this information, at step 450, the TMS treatment plan may be computed. In an example embodiment, the plan may include information regarding optimal coil position, coil orientation, power setting, rate/duration, and a 3-D head model. The TMS delivery plan developed at step 450 may then be provided to a TMS treatment delivery system. It is to be understood that the TMS treatment planning system described herein may be performed using a standard personal computer appropriately programmed, or it may be performed via specialized computers, such as a UNIX workstation or a mainframe computer.

Figure 11:
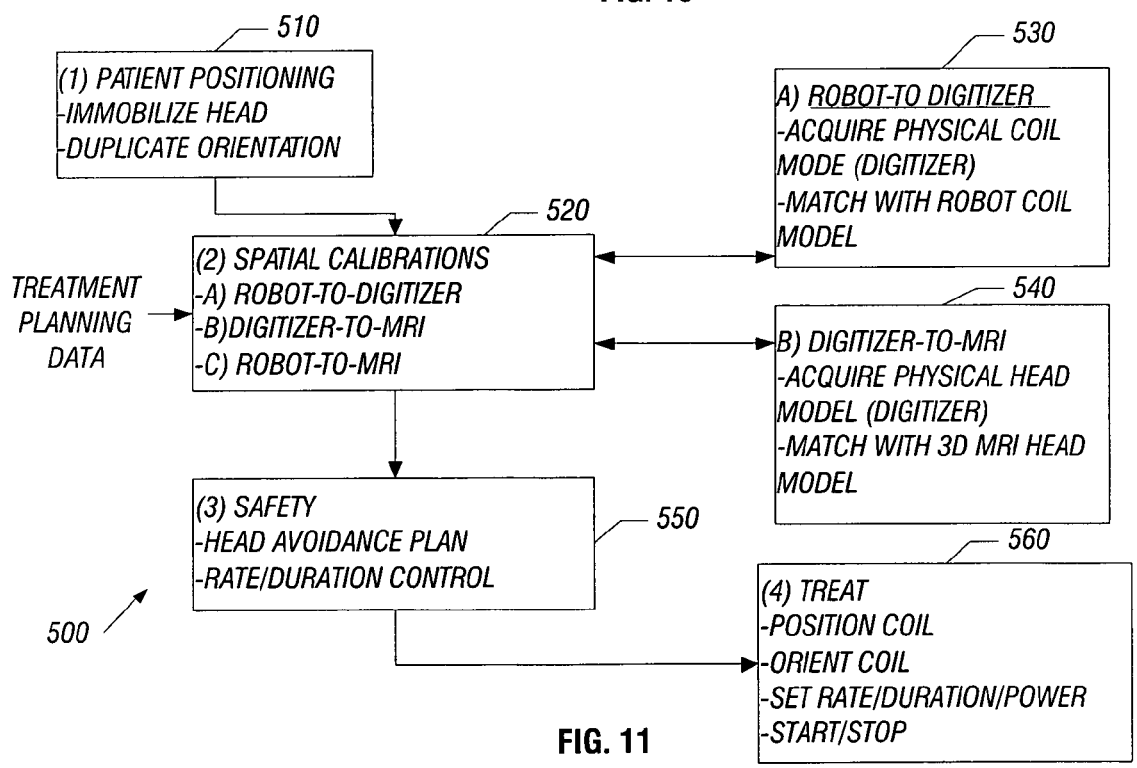
FIG. 11 is a flow diagram of an example TMS treatment delivery system according to the present invention.

FIG. 11 is an example flow diagram of a TMS treatment delivery system according to the present invention. As shown in FIG. 11, an example TMS treatment delivery system 500 may begin at step 510, in which a patent is positioned with his head immobilized so that a duplicate orientation (the same orientation as used for imaging) may be obtained. At step 520, spatial calibrations may be performed utilizing the data provided by the treatment planning system. Spatial calibrations may include, for example, a robot to digitizer calibration, a digitizer to MRI calibration, and a robot to MRI calibration. In an example embodiment, the robot digitizer spatial calibration may be performed at step 530 in which a physical coil model is acquired via a digitizer and is matched with the robot coil model. Key landmarks on the coil body may be used to establish coil x-y-z orientation, the coils' z-axis direction, and the 0,0,0 point on the coil surface. At step 540, the digitizer to MRI calibration may be performed in which a physical head model is acquired via the digitizer and is matched with the 3-D MRI head model provided by the TMS treatment planning system, as discussed above. The robot-to-digitizer and robot-to-MRI transforms may be concatenated to create a robot-to-MRI transform during calibration. Next, at step 550, safety features may be implemented in which a plan for avoidance of the head during movement of the robot is effected. Furthermore, the rate/duration provided by the TMS treatment planning system may be implemented as a control to prevent excess stimulation. Finally, at step 560, TMS delivery is effected after the coil is positioned and oriented and the rate, duration, and power of the delivery is set. The TMS treatment delivery system may be performed using the computing systems discussed above.

In conjunction with the CCCAP disclosed herein, a higher degree of control over the electrical field induced by a TMS coil will improve the value of the experiment/treatment. Such control may be aided by new and inventive coil designs.

Greater control may be had over such features as coil inductance and power dissipation with methods that have been in use for designing gradient coils for magnetic resonance imaging ("MRI") since the late 1980's for cylindrical coils (Turner) and later for planar coils (Martens et al.). These methods involve an inverse technique which allows the magnetic field to be defined at certain points in a volume. This method may be adapted to the design of magnetic stimulation coils which enables the electric field to be defined at certain points. While it is not reasonable to focus the magnetic field at an arbitrary position inside the brain/muscle volume, the resultant coils may provide more focused fields in two dimensions near the brain/muscle surface and with other desirable characteristics such as a lower inductance or a lower heat dissipation.

Suggestions of 10 kHz as the optimum frequency for the stimulation waveform have been made (Davey and Epstein). The stimulation circuit may be considered primarily an LC circuit with a small resistive loss. The capacitive section of the circuit stores energy and when a switch is closed, the energy is transferred to the inductive section, the magnetic stimulation coil, and back to the capacitive section with a frequency $\omega=1/(LC)^{1/2}$. The voltage induced in a conducting body is proportional to this frequency. For the purposes of coil design, the coil is of interest, and thus the capacitive section may be considered constant. Hence, to increase the resonant frequency and the induced voltage, the coil inductance may be lowered.

The target field method may be adapted to provide a coil with a minimum inductance for a given set of electric field constraints. The constraints may be set to provide as smooth a design as possible. The constraints should also be set such the coil is of a reasonable size in order that the natural field falloff moving away from the coil is not too sharp.

The theory behind minimum inductance TMS coils may be adapted from known design techniques for target field gradient coil designs for MRI, such as that of Martens et al, and Turner. For current flowing on a planar surface, the x-y plane, the Fourier transform pair may be defined as:

$$j_x(\alpha, \beta) = \int\int e^{-i\alpha x} e^{-i\beta y} J_x(x, y) dx dz \quad (1.1)$$

and $$J_x(x, z) = \frac{1}{4\pi^2} \int\int e^{i\alpha x} e^{i\beta y} j_x(\alpha, \beta) d\alpha d\beta \quad (2)$$

and similarly for the y-component of the current density. Using:

$$\text{div } J = 0 \quad (3)$$

leads to, at the plane y=a:

$$\alpha j_x(\alpha, \beta) + \beta j_z(\alpha, \beta) = 0 \quad (4)$$

From the vector potential:

$$A(r) = \frac{\mu_0}{4\pi} \int\int_V \frac{J(r')}{|r-r'|} \cdot d^3 x' \quad (5)$$

Orthogonal components may be determined:

$$A_x(r) = \frac{\mu_0}{8\pi^2} \int_{-\infty}^{\infty}\int_{-\infty}^{\infty} \frac{1}{\sqrt{\alpha^2+\beta^2}} \cdot e^{i\alpha x} e^{i\beta y} e^{-\sqrt{\alpha^2+\beta^2} \cdot z} j_x(\alpha,\beta) d\alpha d\beta \quad (6)$$

$$A_y(r) = \frac{\mu_0}{8\pi^2} \int_{-\infty}^{\infty}\int_{-\infty}^{\infty} \frac{1}{\sqrt{\alpha^2+\beta^2}} \cdot e^{i\alpha x} e^{i\beta y} e^{-\sqrt{\alpha^2+\beta^2} \cdot z} j_y(\alpha,\beta) d\alpha d\beta \quad (7)$$

and $$A_z(r) = 0. \quad (8)$$

The electric field in a homogeneous media may be written as:

$$E = -\frac{\partial A}{\partial t} \quad (9)$$

and so for a sinusoidal current, $I = I_0 \sin \omega t$, $$E_x(r) = A_x(r) \omega \cos \omega t \text{ etc.} \quad (10)$$

If the x-component of the E-field is considered:

$$|E_x| = \omega \cdot A_x \quad (11)$$

and so $$|E_x| = \omega \frac{\mu_0}{8\pi^2} \int_{-\infty}^{\infty}\int_{-\infty}^{\infty} \frac{1}{\sqrt{\alpha^2+\beta^2}} e^{i\alpha x} e^{i\beta y} e^{-\sqrt{\alpha^2+\beta^2} \cdot z} |j_x(\alpha,\beta)| d\alpha d\beta \quad (12)$$

The electric field must be symmetric in both the x and y directions, so that the imaginary components in the above equation can be reduced to $\cos(\alpha x)$ and $\cos(\beta y)$. The energy from the current density plane may be calculated from:

$$W = \frac{1}{2}\int_V A \cdot J d^3 x \quad (13)$$

leading to:

$$W = \frac{\mu_0}{16\pi^2} \iint \frac{d\alpha d\beta}{\sqrt{\alpha^2+\beta^2}}\left(1+\frac{\alpha^2}{\beta^2}\right)|j_x(\alpha,\beta)|^2 \quad (14)$$

In order to minimize W subject to a set of electric field constraints, the error function may be formed:

$$U[j_x^a(\alpha,\beta)] = W - \sum_{j=1}^{N} \lambda_j [E(r_j) - E^t(r_j)] \quad (15)$$

where $\lambda_j$ are Lagrange multipliers and the electric field at points $r_j$ is constrained to have the values $E^t(r_j)$. Setting:

$$\frac{\partial U}{\partial j_x^a(\alpha,\beta)} = 0 \quad (16)$$

gives:

$$j_x(\alpha,\beta) = \frac{\beta^2}{\alpha^2+\beta^2}\sum_{j=1}^{N} \lambda_j \cos(\alpha x_j) \cos(\beta y_j) e^{(-z_j)\sqrt{\alpha^2+\beta^2}} \quad (17)$$

The Lagrange multipliers are found by solving the matrix equation:

$$E^t(r_j) = \sum_{j=1}^{N} C_{ij} \lambda_j \quad (18)$$

for $i = 1, N$ found by substituting the current density equation into the electric field equation. Once the current density has been calculated, the Fourier transform may be used to obtain the current density $J_x(x,z)$ and $J_z(x,z)$. These may then be integrated to provide a stream function and may be discretized into current loops. The inductance may be estimated using $W=0.5*L.I^2$. The accuracy of the design is then dependent on the number of loops chosen to approximate the continuous current density. The design can then be checked using:

$$E = -j\omega \cdot \frac{\mu_0 I}{4\pi} \oint \frac{dl}{R} \quad (19)$$

and summing individual wire elements to obtain the total field distribution. The coil may also be evaluated in the presence of conducting boundaries to simulate a human head using numerical methods such as finite element analysis. The design process does not take into account these boundaries, although an approximation may be incorporated into the design using a conducting sphere and a well-known method of calculating electric field in a spherical volume, as set forth in Eaton (1992).

To obtain a varying electric field, the symmetries may be adjusted, i.e. all $\cos(\alpha x)$ need to be changed to $\sin(\alpha x)$.

To achieve a minimum power design, the above calculation may be used, but replacing the energy term with the following:

$$P = \frac{\rho}{2t} \int_{-\infty}^{\infty} \int_{-\infty}^{\infty} \frac{\alpha^2+\beta^2}{\beta^2} j_x^2(\alpha,\beta) d\alpha d\beta \quad (20)$$

Recent studies have suggested that rapid stimulation (>1 Hz) may enhance the potency of magnetic stimulation. For situations involving rapid stimulation, heating of the coil becomes an issue due to the increased duty cycle. While cooling mechanisms have been employed it is also advantageous to include in the coil design a power dissipation term, in order for heating to be minimized. Minimum power designs are larger and generally smoother than minimum inductance designs.

When attempting TMS, unwanted stimulation of the nerves in the scalp may occur for persons with high thresholds (usually meaning a slightly thicker skull), possibly causing pain and facial twitching, confounding experimental results. With the addition of negative turns to the windings of the stimulator coil, and a small spacing between the coil and the scalp, the fields across this area may be reduced significantly. However, this comes at the expense of some focusing ability, and coil inductance and heating.

Figure 12:
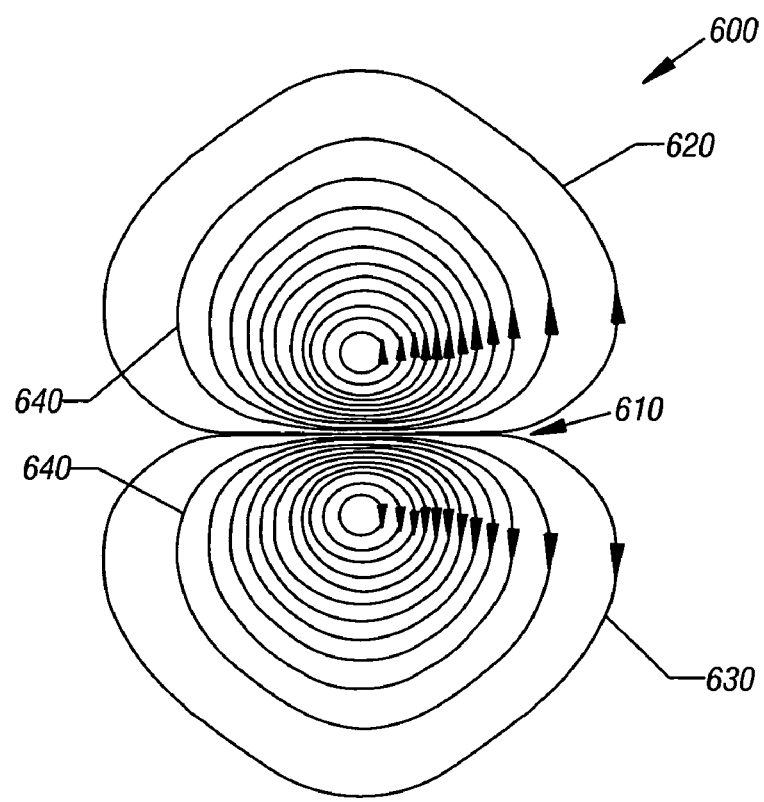
FIG. 12 is a representation of a TMS coil in accordance with the present invention.

FIG. 12 shows an example embodiment of a coil design developed by an inverse method. As shown in FIG. 12, coil 600 is a two-winged coil design having a first wing 620 and a second wing 630. The wings extend peripherally from a center portion 610. As can be seen in FIG. 12, coil 600 is a variation of a figure-eight coil design. The coil 600 varies from such a standard design, in that the individual wire elements or windings 640 that make up the coil are closely concentrated towards the center portion 610 and extend therefrom in increasing arcs to the periphery of the coil. As shown in FIG. 12, the direction of the electric field traveling through the windings 640 is opposite directions for each of the two wings of the coil. However, the windings 640 making up each of the wings 620 and 630 all travel in the same direction.

The spacing between windings 640 may vary in given embodiments. As shown in FIG. 12, there are approximately 12 wires in each wing of the coil. However, it is to be understood that more or fewer windings may be present in a given design. Further, the wings 620 and 630 are generally shown as mirror opposites. However, it is to be understood that in certain embodiments, the wings may have different eccentricities.

The coil may be designed in accordance with standard practices for coil manufacture well-known to those with skill in the art. In an example embodiment, the windings may comprise copper or another conducting material, such as silver (or other conducting material) ribbon placed on its edge. Such wire may have a diameter of between about 0.1 and 1.0 millimeters in example embodiments. Furthermore, the coil may be encased in plastic or another non-conducting material in order for reasons of safety and other issues. In certain embodiments, the coil may be encased in thermally conductive epoxy to enhance heat dissipation. Further, the coil may be encased with a water, oil or air cooling system. Coils may also be wound in layers placed directly upon one another, and connected in series or parallel. The wire pattern may be transferred to a sheet former for construction using a computerized milling machine, or may be transferred using heat from an inked hard copy, such as a computer printout. The wire pattern may be constructed from one single wire/ribbon wound with small connecting paths between loops. Standard connections from the coil to cabling necessary to adapt the coil to a magnetic stimulator may be made.

The method may be changed slightly to provide a minimum inductance configuration providing a spatial gradient in the electric field for peripheral nerve stimulation. An example of this is shown in FIG. 13.

Figure 13:
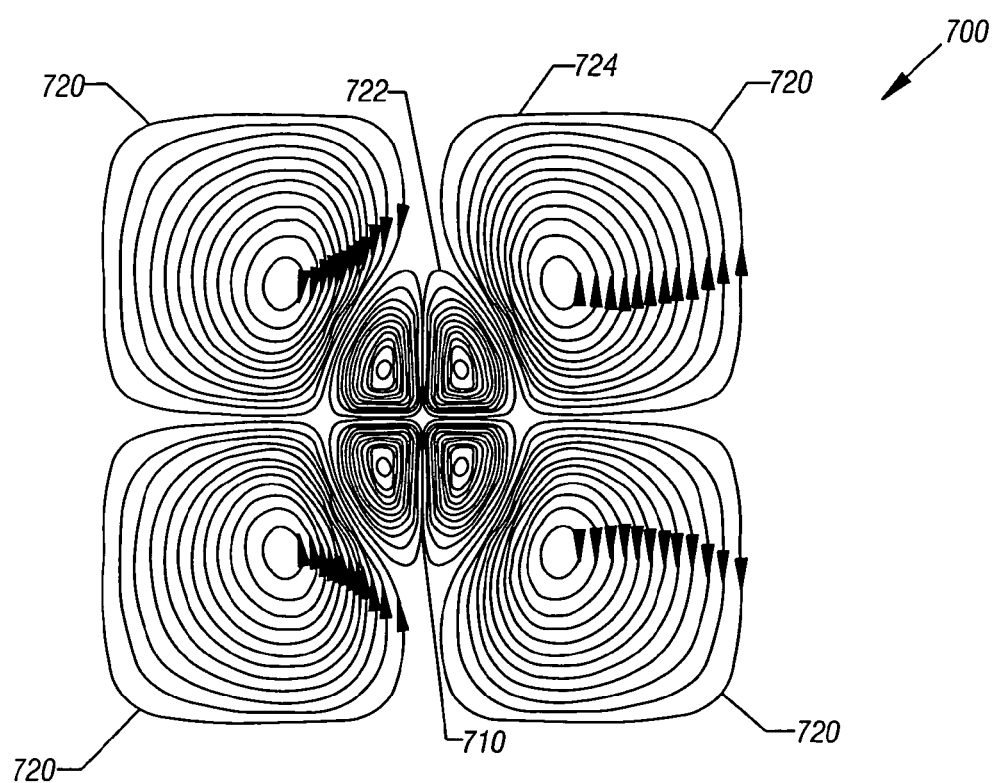
FIG. 13 is a representation of a TMS coil in accordance with the present invention.

FIG. 13 is a top view of an alternate coil design according to the present invention. As shown in FIG. 13, coil 700 is a four-winged coil having four wings 720. Each of the wings 720 has a first set of windings 722 and a second set of windings 724. As seen in FIG. 13, each of the wings 720 is generally a variation of a figure-eight coil, in which the more centrally located portion 722 is smaller than the peripherally located portion 724. This coil may be designed similarly to coil 600 discussed above, in that each of the portions of each wing 720 may be designed so that the windings are concentrated more closely towards the interior portion of the coil and extending therefrom in increasing arcs. This is especially the case for the peripheral portion 724.

In certain embodiments, it may be desirable for the coil to be designed in a generally square manner. The coil shown at FIG. 13 may be constructed in accordance with well-known principles for coil manufacture, as discussed above.

Figure 14:
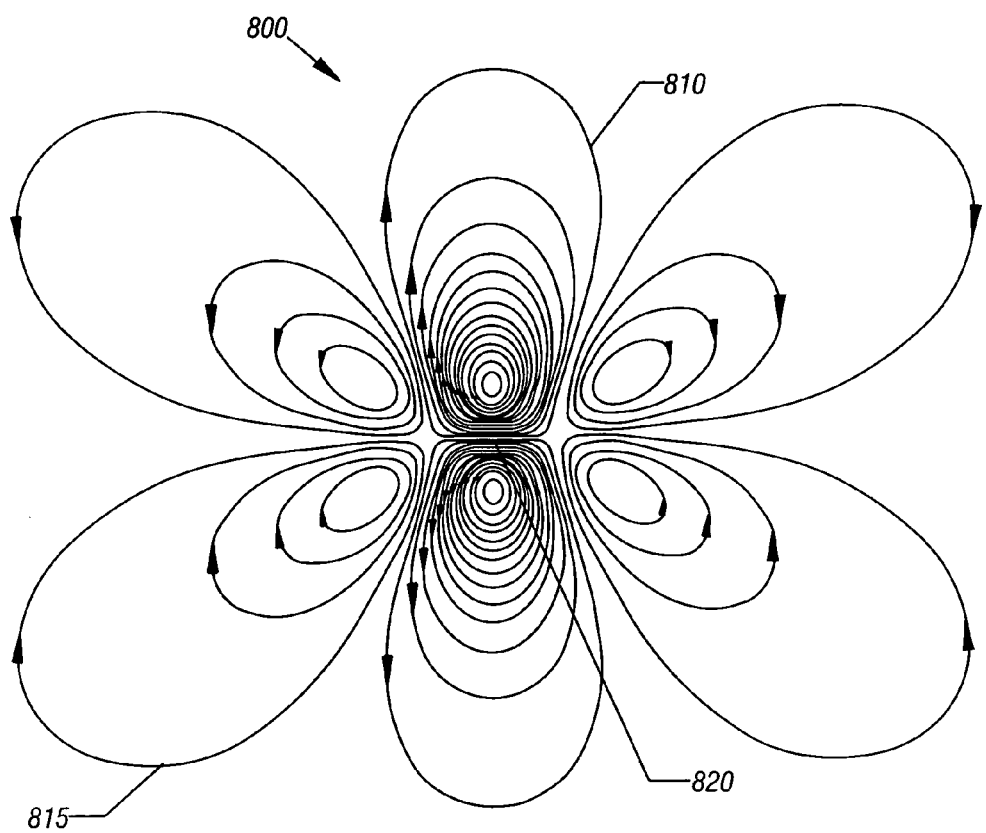
FIG. 14 is a diagram of an alternate coil embodiment according to the present invention.

FIG. 14 is a diagram of another coil embodiment created by an inverse design method. As shown in FIG. 14, coil 800 is a 6-winged coil having two central windings 810 and four outer windings 815 in which the outer windings 815 extend peripherally from center portion 820 in increasing arcs. This coil was designed using constraints on the x-component of the electric field. In an example embodiment, the coil dimensions may be approximately 36 cm (x-direction) by 28 cm (y-direction), substantially larger than the B-shaped coil. However, it should be noted that in other embodiments, the current density may be apodized (basically, outside a certain region the current density may be multiplied by an exponential function so that the outer rings are effectively shrunk). The electric field may then be recalculated to determine the significance of the effect.

The constraints in this embodiment were set such that the x-component of the electric field at the center point was twice that of a point at 2.5 cm along the x and y axes and 3 cm from the coil. That is, the constraints were:

| x(cm) | y | z | E-field (V/m) |
|---|---|---|---|
| 0.0 | 0.0 | 3.0 | 100 |
| 2.5 | 1.1 | 3.0 | 50 |
| 0.0 | 2.5 | 3.0 | 50 |

Figure 15:
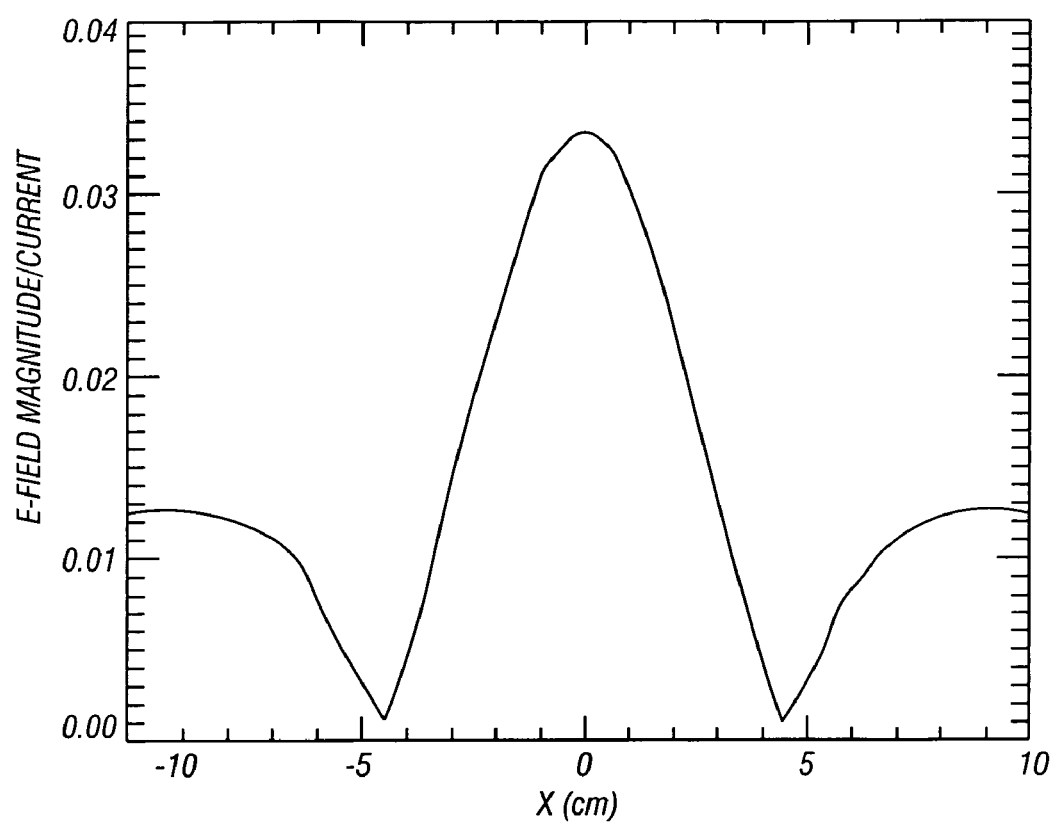
FIG. 15 is a graphical representation of the electric field magnitude/current of the coil of FIG. 14 along the x-axis.
Figure 16:
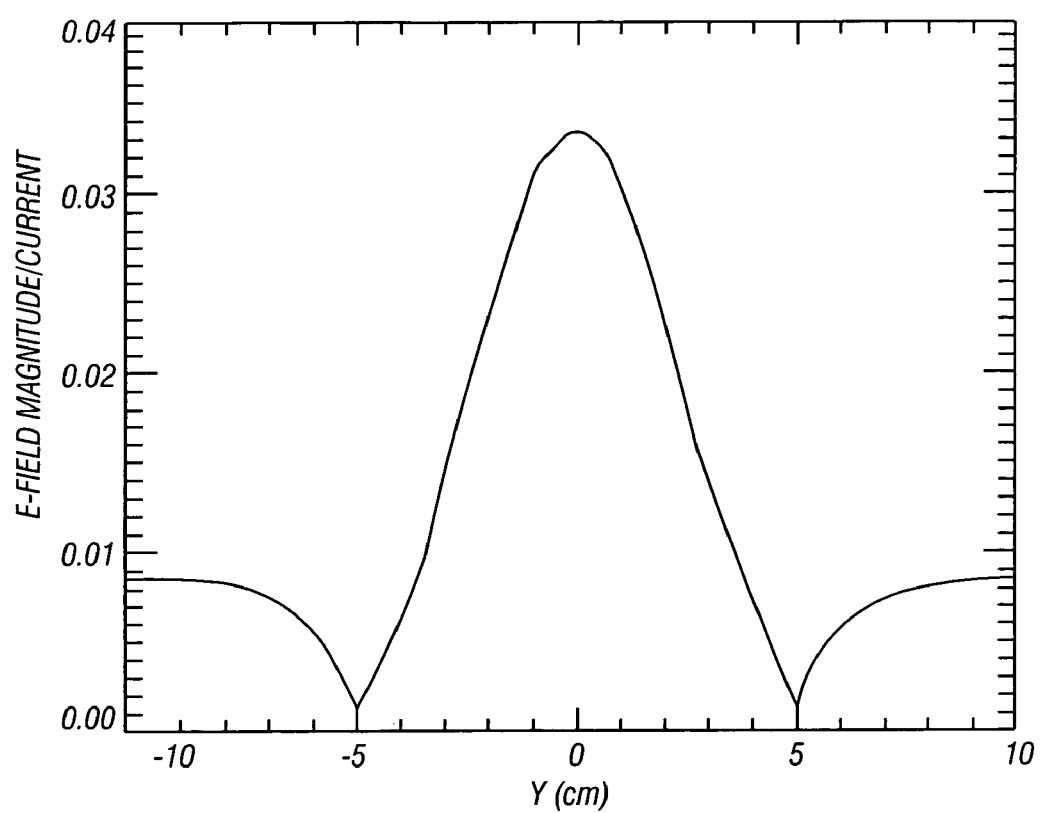
FIG. 16 is a graphical representation of the electric field magnitude/current of the coil of FIG. 14 along the y-axis.

FIGS. 15 and 16 are graphical representations of the electric field magnitude/current along the x and y axes, respectively. The current required to obtain a field of 100 V/m at the central point was 2951 amps, assuming an excitation waveform frequency of 5 Khz. The coil inductance was estimated to be 20 uH. The three constraints (one at the center, one each on +x and y axes) represent an attempt to localize the generated field inside a given region. Other constraints (-x and y axes) are implied by symmetry. The four outer windings 815 serve to limit the extent of the field in the x-direction. The central windings 810 provide the main field generation and limit the field extent in the y-direction. Further, the smooth spreading of the wire paths serves to reduce mutual inductances between wires.

Figure 17:
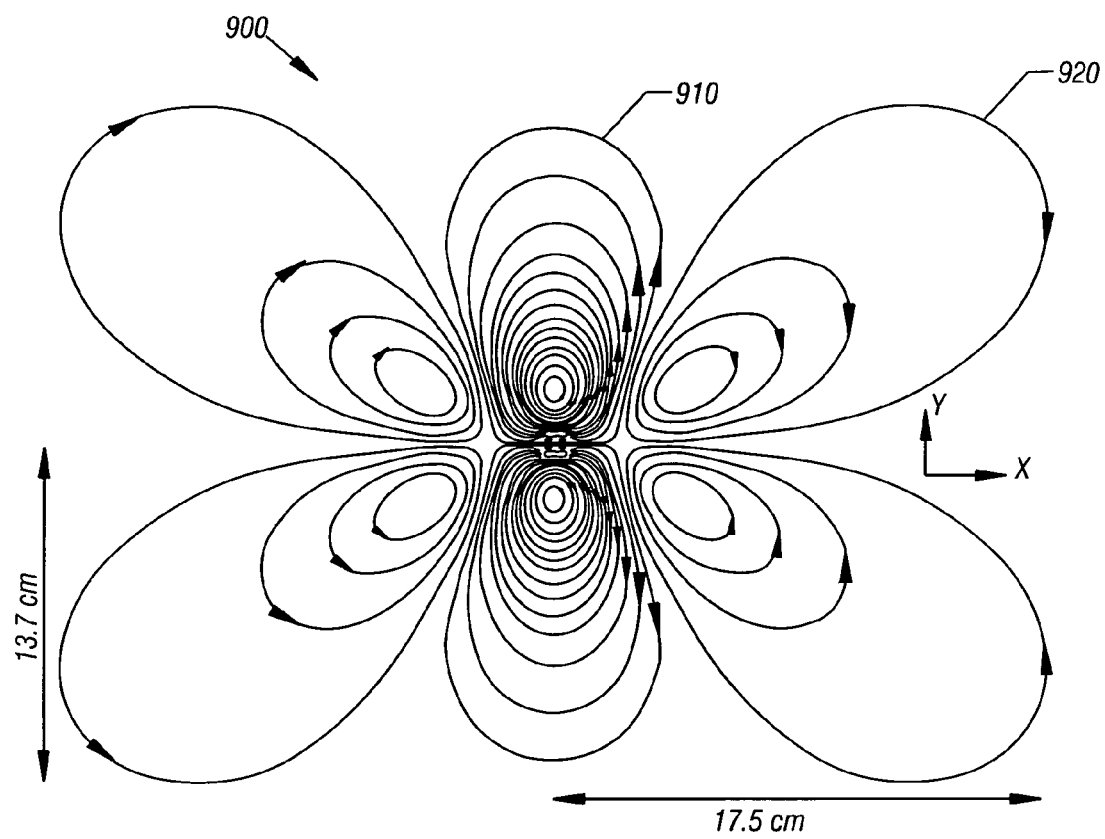
FIG. 17 is a diagram of an alternate coil embodiment according to the present invention.
Figure 18:
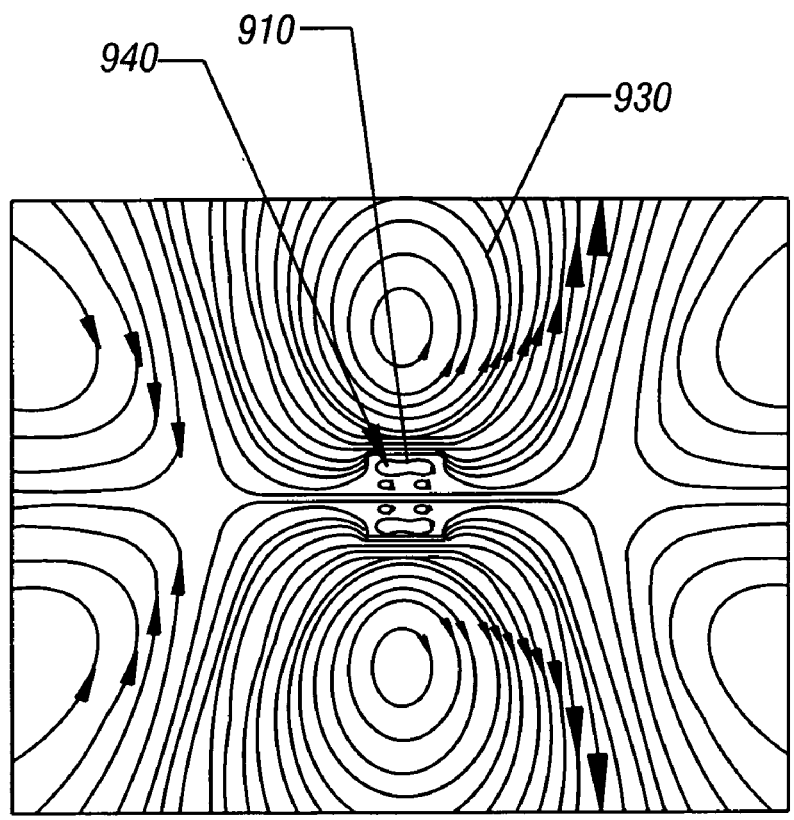
FIG. 18 is a close up view of the center portion of the coil shown in FIG. 17.

FIG. 17 is a diagram of an alternate coil embodiment. As shown in FIG. 17, coil 900 is a 6-winged coil having two central coils 910 and four outer coils 920. The coil of FIG. 17 differs from the coil of FIG. 14 in that the central coils 910 include several negative turns in order to reduce the magnitude of the electric field. The negative turns are shown more specifically in FIG. 18, which is a close up of the central coils 910. As shown in FIG. 18, the central coils 910 include a plurality of first turns 930 and a plurality of second turns 940. As shown in FIG. 18, the second turns 940 are configured in the opposite direction and carry current having the opposite polarity of the current carried by the first turns 930. Although shown in FIG. 18 as having three negative turns, it is to be understood that in other embodiments more or fewer negative turns may be present in a given coil design. The constraints were the same as the coil for FIG. 14, except for an extra constraint at x=y=z=0.5 cm, to reduce the magnitude of the electric field at a distance of 0.5 cm from the coil. This extra constraint resulted in a coil that reduced the ratio of the maximum value of the calculated electric field in a plane 5 mm from the coil to that in the desired stimulation area (3 cm away from the coil at the center) by 18%. The current needed to create the same field of 100 V/m is 3425 A as opposed to 2951 for the coil of FIG. 14. The coil focusing properties are similar to that of FIG. 14.

It is to be understood that in certain embodiments, the negative turns may be located in a separate layer from turns having an opposite polarity. For example, small secondary coil, consisting of a few turns of either a figure 8 design, or a smaller version of the target field designs disclosed herein, may be placed next to the magnetic stimulation coil such that the center of the coils are coincident but such that the distance between them is adjustable. The current may flow in the second coil such that the electric field generated by the current pulse is opposing the direction of the field produced by the main coil. Further, the angle that the loops make to the surface of the coil may also be adjusted.

It is to be understood that the coil designs disclosed herein may be used independently from the delivery methods herein. Further, it is to be understood that the delivery methods disclosed may be used independently from the coils herein.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims.

REFERENCES

The following references, to the extent that they provide exemplary procedural or other details supplementary to those set forth herein, are specifically incorporated herein by reference.

Cadwell, J. Optimizing magnetic stimulator design. Magnetic Motor Stimulation: Basic Principles and Clinical Experience. (EEG Suppl. 43) 238–248, 1991.

Carbunaru, R. and Durand, D. M. Toroidal coil models for transcutaneous magnetic stimulation of nerves. IEEE Trans Biomedical Eng. 48(4):434–441 (April, 2001).

Davey, K. and Epstein C. M. Magnetic stimulation coil and circuit design. IEEE Trans Biomedical Eng. 47(11): 1493–1499 (November 2000).

Lin et al. Magnetic coil design considerations for functional magnetic stimulation. IEEE Trans Biomedical Eng. 47:600–611 (May, 2000).

Martens, M. A. et al. Insertable biplanar gradient coils for magnetic resonance imaging. Rev Sci Instrum. 62(11) 2639–2645. (November, 1991).

Ruohonen, J. et al. Coil optimization for magnetic brain stimulation. Ann Biomed Eng. September–October 1997; 25(5):850–9.

Turner, R. A target field approach to optimal coil design. J.Phys. D: Appl. Phys. 19:L147–151 (1986).

Turner, R. Minimum inductance coils. J.Phys. E. 21:948–952 (1988).

Roth, B. J., Balish, M., Gorbach, A., and Sato, S. (1993). How well does a three-sphere model predict positions of dipoles in a realistically shaped head? *Electroenceph. clin. Neurophysiol.*, 87: 175–184.

Yvert, B., Bertrand, O., Echallier, J. F., Pernier, J. (1995). Improved forward EEG calculations using local mesh refinement of realistic head geometries. *Electroenceph. clin. Neurophysiol.*, 95: 381–392.

Dipole localization in patients with epilepsy using the realistically shaped head model. *.Electroenceph. clin. Neurophysiol.*, 102: 159–166.

Amassian V E, Cracco R Q, Maccabeee P J, Cracco J B, Rudell A, Eberle L. (1989) Suppression of visual perception by magnetic coil stimulation of human occipital cortex. EEGCNP 74:458–462.

Artola A, Brocher S, Singer W. (1990) Different voltage dependent thresholds for inducing long-term depression and long-term potentiation in slices of rat visual cortex. Nature 347:69–72.

Baker-Price, L. A., Persinger, M. A. (1996) Weak but complex pulsed magnetic fields may reduce depression following traumatic brain injury. Perceptual and Motor Skills 83:491–498.

Barker A T, Freeston I L, Jalinous R, Jarratt J A (1987) Magnetic stimulation of the human brain and peripheral nervous system: An introduction and results of an initial clinical evaluation. Neurosurgery 20:100–109.

Barker A T, Jalinous R, Freeston Ill. (1985) Non-invasive magnetic stimulation of human motor cortex. Lancet 1106–1107.

Baxter L R, Schwartz J M Phelps M E et al. (1989) Reduction of prefrontal cortex glucose metabolism common to three types of depression Arch Gen Psych 46:243–250.

Beckers G, Zeki S. (1995) The consequences of inactivating areas V1 and V5 on visual motion perception. Brain 118: 49–60.

Bench C J, Friston K J, Brown R G, et al. (1992) The anatomy of melancholia-focal abnormalities of cerebral blood flow in major depression. Psychol Med 22:607–615.

Bevington P R, Robinson D K (1992). *Data reduction and error analysis for the physical sciences*. McGraw-Hill Inc., New York, pp. 38–52.

Bickford R G, Fremming B D (1965) neuronal stimulation by pulsed magnetic fields in animals and man. Dig 6th Int Conf Med Electronics Biol Eng. p 112.

Bookheimer S Y, Zeffior T A, Blaxton T, et al. (1997) A direct comparison of PET activation and electrocortical stimulation mapping for language localization. Neurology 48: 1056–1065.

Brasil-Neto J P, McShane L M, Fuhr P, Hallett M, and Cohen L G. (1992) Topographic mapping of the human motor cortex with magnetic stimulation: factors affecting accuracy and reproducibility. EEGCNP 85: 9–16.

Bridgers S L, Delaney R C (1980) Transcarnial magnetic stimulation: an assessment of cognitive and other cerebral effects.

Castleman K (1996). *Digital Image Processing*. Prentice Hall, Upper Saddle River, N.J.

Chan C Y, Nicholson C. (1986) Modulation by applied electric fields of purkinje and stellate cell activity in the isolated turtle cerebellum. J Physiol 371:89–114.

d'Arsonval A. (1896) Dispositifs pour la mesure des courants alternatifs de toutes frequences. C R Soc Biol 3:450–457.

Davey K R, Cheng C H, Epstein C M (1991) Prediction of magnetically induced electrical fields in biologic tissue. IEEE Transactions on Biomedical Engineering 38:418–422.

Day B L, Dressler D, Maertens de Noordhout A, et al. (1989) Electric and magnetic stimulation of human motor cortex: surface EMG and single motor unit responses. J Physiol (Lond) 412–449–73.

Desmond J E, Sum J M, Wagner A D et al. (1995) Functional MRI measurement of language lateralization in Wada-tested patients. Brain 118: 1411–1419.

Dhuna, A. K., Gates, J. R., Pascual-Leone, A. (1991), Transcranial magnetic stimulation in patients with epilepsy. Neurology 41:1067–1071.

Eaton H. Electric field induced in a spherical volume conductor from arbitrary coils: application to magnetic stimulation and MEG. Med Biol Eng Comp 1992;30:433–440.

Epstein C M, Schwartzberg D G, Davey K R, Suderth D B. (1990) Localizing the site of magnetic brain stimulation in humans. Neurology 40:666–670.

Epstein, C. M., Lah, J. J., Meador, K., Weissman, J. D., Gaitan, L. E., & Dihenia, B. (1996). Optimum stimulus parameters for lateralized suppression of speech with magnetic brain stimulation. Neurology 47:1590–3.

Fauth, C., Meyer, B. -U., Prosiegle, M., Zihl, J., Conrad, B. (1992) Seizure induction and magnetic brain stimulation after stroke. Lancet 339:362.

Fox PT (1995) Spatial normalization: origins, objectives, applications and alternatives. Human Brain Mapping 3: 161–164.

Fox P T, Burton H, Raichle M E (1987) Mapping human somatic sensory cortex with positron emission tomography. J Neurosurgery 63: 34–43.

Fox P T, Ingham R J, Ingham J C, Hirsch T B Downs J H, Martin C, Jerabek P, Glass T, Lancaster J L (1996) A PET study of the neural systems of stuttering. Nature 382: 158–162.

Fox P T, Ingham R J, Mayberg H, George M, Martin C, Ingham J, Robey J, Jerabek P. (1997) Imaging human cerebral connectivity by PET during TMS. Neuroreport 8: 2787–2791

Fox P T, Mintun M A (1989) Noninvasive functional brain mapping by change-distribution analysis of averaged PET images of $H_2^{15}O$ tissue activity. J Nucl Med 30: 141–149.

Fox P T, Mintun M A, Reiman E M, Raichle M E (1988) Enhanced detection of focal brain responses using inter-subject averaging and change-distribution analysis of subtracted PET images. J Cereb Blood Flow Metab 8: 642–653.

Fox P T, Parsons L M, Lancaster J L (1998) Beyond the single study: function-location metanalysis in cognitive neuroimaging. Current Opinions in Neurobiology 4: in press.

Fox P T, Perlmutter J S, Raichle M E (1985) A stereotactic method of anatomical localization for PET. JCAT 9: 141–153.

Fried I, Nenov V I, Ojemann S G, Woods R P (1995) Functional MR and PET imaging of rolandic and visual cortices for neurosurgical planning. J Neurosurg 83: 854–861.

Fritsch G and Hitzig E (1870) Uber die elektrische Erregbarkeit des Frosshirns. Translation by G. von Bonin. In The Cerebral Cortex, pp. 73–96. Thomas, Springfield, Ill., USA Geller, V., Grisaru, N., Abarbanel, J. M. Lemberg, T. Belmaker, R. H. (1997) Slow magnetic stimulation of prefrontal cortex in depression and schizophrenia. Progress in Neuro-Psychopharmacology and Biological Psychiatry 21:105–110.

Gerloff C, Corwell B, Chen R, Hallett M, Cohen L G (1997) Stimulation over the human supplementary motor area interfers with the organization of future elements in complex motor sequences. Brain 120:1587–1602.

Gisaru N Yaroslavsky U, Abarbanel J et al. (1994) Transcranial magnetic stimulation in depression and schizophrenia. Eur Neuropsychopharm 4: 287–88.

Goddard G V (1967) Development of epileptic seizures through brain stimulation at low intensity. Nature 214: 1020–1021.

Goddard G V, McIntyre D C, Leeck C K. (1969) A permanent change in brain function resulting from daily electrical stimulation. Exp Neurol 25:295–330.

Gonzales R C, Woods R E (1992). *Digital Image Processing*. Additon-Wesley, Reading, Mass.

Gormal A L F (1966) Differential patterns of activation of the pyramidal system elicited by surface anodal and cathodal cortical stimulation. (1966) J Neurophysiol. 29:547–564.

Grafman J, Pascual-Leone A, Alway D, Nichelli P, Gomez-Tortosa E, Hallett M. (1994) Induction of a recall deficit by rapid-rate transcranial magnetic stimulation. NeuroReport 5:1157–1160.

Green, R M, Pascual-Leone, A, Wasserman, E M (1997) Ethical guidelines for rTMS research, IRB 19:1–7

Gustafsson, B., and Wigstrom, H. Physiological mechanisms underlying long term potentiation. Trends Neurosci 1988, 11:156–162.

Hem J E C, Landgren S, Phillips C G and Porter R. (1962) Selective excitation of cortico fugal neurons by surface stimulation ob the baboon's motor cortex. J Physiol (Lond) 161:73–99

Hess C W, Mills K R and Murray N M F (1987) Responses in small hand muscles from magnetic stimulation of the human brain. J Physiol (London) 388:397–419.

Hoflich G, Kasper S, Hufnagel et al. (1993) Application of transcranial magnetic stimulation in treatment of drug resistant major depression. (1993) Hum Psychopharmacol 8: 361–65.

Homberg, V., Netz, J. (1989) Generalised seizures induced by transcranial magnetic stimulation of motor cortex (letter). Lancet II:1223.

Hubel D H, Wiesel T N (1979) Brain mechanisms of vision. Sci Am 241: 150–162.

Hufnagel, A. Elger, C. E., Klingmuller, D. et al., (1990) Activation of epileptic foci by transcranial magnetic stimulation: effects on secretion of prolactin and lutenizing hormone. Journal of Neurology 237:242–246.

Ingham R J, Fox P T, Ingham J C, Zamarripa F, Martin C, Jerabek P, Cotton J. (1996) Functional lesion investigation of developmental stuttering with positron emission tomography. J Speech and Hearing Research 39: 1208–1227.

Iriki A, Pavlides C, Keller A, et al. (1991) Long-term potentiation of thalamic input to the motor cortex induced by coactivation of thalamocortical and corticocortical infarcts. J Neurophysiology 65:1435–1441.

Jack C R, Thompson R M, Butts R K et al. (1994) Sensory motor cortex: correlation of presurgical mapping with functional MR imaging and invasive cortical mapping. Neuroradiology 190: 85–92.

Jennum P, Friberg L, Fuglsang-Frederiksen A, Dam M. (1994) Speech localization using repetitive transcranial magnetic stimulation. Neurol 44:269–273.

Jones E G (1981) Anatomy of cerebral cortex: columnar input-output organization. In, The Organization of Cerebral Cortex, Schmitt F O, Worden F G, Adelman G, Dennis S G (Eds), MIT Press, Cambridge Mass.

Jones E G Wise S P (1978) Size, laminar and columnar distributions of efferent cells in the sensory-motor cortex of monkeys. J Comp Neuro 175:391–438.

Kandel E, Schwartz J H, Jessell T M (1991) Principles of Neural Science. pg 166–167.

Kandler, R. (1990) Safety of transcranial magnetic stimulation. Lancet 335:469–470.

Kolbinger H M, Hoflich G, Hufnagel A et al. (1995) Transcranial magnetic stimulation (TMS) in the treatment of major depression: a pilot study. Human Psychoopharmacol 10: 305–310.

Krings T, Buchbinder B R, Butler W E et al. (1997) Stereotactic transcranial magnetic stimulation: correlation with direct electrical cortical stimulation. Neurosurgery 41: 1319–1326.

Lancaster J L, Fox P T, Downs J H, Nickerson D, Hander T, El Mallah M, Zamarripa F (1997). Global spatial normalization of the human brain using convex hulls. *J of Nucl Med,* 40:942–955.

Lancaster J L, Glass T G, Lankipalli B H, Downs H, Mayberg H, Fox P T (1999). A modality-independent approach to spatial normalization of tomographic images of the human brain. *Human Brain Mapping* 3:209–223.

Landau W, Bishop G H, Clare M H. Site of excitation in stimulation of the motor cortex. (1965) J Neurophysiol 28:1206–1222.

Landgren S, Phillips C G, Poerter (1962) Cortical fields of origin of the monosynaptic pyramidal pathways to some alpha motoneurons of the baboon's hand and forearm. J Physiol (Lond) 161:112–151.

LeBlanc R, Meyer E (1990) Functional PET scanning in the assessment of cerebral arteriovenous malformations. J Neurosurg 73: 615–619.

Lemen, L. C., Woldorff, M. G., Seabolt, M., Gao, J. H., Fox, P. T. (1998) Neuronal stability in prolonged visual stimulation. *Electroenceph.and Clin. Neurophysiology,* in press.

Liotti, M. L., Ryder, K., Woldorff, M. G. (1998) Auditory attention in the congenitally blind: where, when, and what gets reorganized. *Neuroreport*, in press.

Liu Y J, Pu Y, Gao J -H, Parons L M, Xiong J, Liotti M, Bower J M, Fox P T. (1998)Human red nuclues and lateral cerebellum in cooperative roles supporting sensory discrimination. Neuron: in review Maldjian J, Atlas S W, Howard R S, et al. (1996) Functional magnetic resonance imaging of regional brain activity in patients with intracerebral arteriovenous malformations before surgical or endovascular therapy. J Neurosurg 84: 477–483.

Martin J H (1991) The collective electrical behavior of cortical neurons: the electroencephalogram and the mechanisms of epilepsy. In, *Principles of neural Science*, Kandel E R, Schwartz J H, Jessel T M (Eds) Elsevier; New York Martinot J L, Hardy P, Feline A et al. (1990) Left prefrontal glucose metabolism in the depressed state: a confirmation. Am J Psych 147:1313–1317.

Mayberg H. Limbic-cortical dysregulation: a proposed model of depression. (1997) J Neuropsychiatry and clinical neurosciences. 9:471–481.

Mayberg H. Frontal lobe dysfunction in secondary depression. (1994) Journal of Neuropsychiatry and Clinical Neurosciences 6:428–442.

Mayberg H S, Brannan S K, Mahurin R K et al. (1997) Cingulate function in depression: a potential predictor of treatment response.

Mayberg H S, Lewis P J, Regenold W, et a. (1994) Paralimbic hypoperfusion in unipolar depression. J Nucl Med 35:929–934.

Mayberg H S, Starksetin S E, Peyser C E, et al. (1992) Paralimbic frontal lobe hypometabolism in depression associated with Huntington's disease. Neurology 42:1791–1797

Mayberg H S, Starksetin S E, Sadzot B, et al. (1990) Selective hypometabolism in depression associated with Parkinson's disease. Ann Neurol 28:57–64.

McNaughton, B. L. (1982) Long-term synaptic enhancement and short term potentiation in rat fascia dentata act through different mechanisms. J. Physiol. (London) 324: 249–262.

Michelucci, R., Valzania, F., Passarelli, D., Santangelo, M., Rizzi, R., Buzzi, A. M., Tempestini, A., Tassinari, C. A. (1994) Rapid-rate transcranial magnetic stimulation and hemispheric language dominance: Usefulness and safety in epilepsy. Neurology 44:1697–1700.

Mills K R, Boniface S J, Shubert M (1992) Magnetic brain stimulation with a double coil: the importance of coil orientation. EEGCNP 85: 17–21, Motluck A. Cutting out stuttering (1997) New Scientist 2:32–35.

Ojemann G, Ojemann J, Lettich E, et al. (1989) Cortical language localization in left, dominant hemisphere. An electrical stimulation mapping investigation in 117 patients. J Neurosurg 71:316–326.

Pardo J V, Fox P T (1993) Preoperative assessment of the cerebral hemispheric dominance for language with CBF PET. Human Brain Mapping 1: 57–68.

Parsaye K, Chignell M, Khoshafian S, Wong H (1989). *Intelligent Databases: Object-oriented, deductive hypermedia technologies*. John Wiley & Sons, Inc., New York, pp 30–31.

Pascual-Leone A, Catala M D. (1996) Lateralized effect of rapid-rate transcranial magnetic stimulation of the prefrontal cortex on mood. Neurol 46:499–502.

Pascual-leone A, Gates J F, Dhuma Anil. (1991) Induction of speech arrets and counting errors with rapid-rate transcranial magnetic stimulation. Neurol 41:697–702.

Pascual-Leone A, Gomez-Tortosa E, Grafman J, Alway D, Nichelli P, Hallett M. (1994) Induction of visual extinction by rapid-rate transcranial magnetic stimulation of parietal lobe. Neurol 44:494–498.

Pascual-Leone A, Rubio B, Pallardo F, Catala M D. (1996) Rapid-rate transcranial magnetic stimulation of left dorsolateral prefrontal cortex in drug-resistant depression. Lancet 348:233–237.

Pascual-Leone A, Valls-Sole J, Brasil-Neto J P, Cohen L G, Hallett M (1994) Akinesia in Parkinson's disease. I. Shortening of simple reaction time with focal, single-pulse transcranial magnetic stimulation. Neurology 44: 884–891.

Pascual-Leone, A., Gates, J. R., Dhuna, A. (1991) Induction of speech arrest and counting errors with rapid-rate transcranial magnetic stimulation. Neurology 41:697–702.

Pascual-Leone, A., Houser, C. M., Reese, K., Shotland, L. I., Grafman, J., Sato, S., Valls-Sole, J., Brasil-Neto, J. P., Wasserman, E. M., Cohen, L. G., & Hallett, M. (1993). Safety of rapid-rate transcranial magnetic stimulation in normal volunteers. Electroencephalography and Clinical Neurophysiology 89: 120–130.

Pascual-Leone, A., Rubio, B., Pallardo, F., Catala, M. D. (1996) Rapid-rate transcranial magnetic stimulation of left dorsolateral prefrontal cortex in drug-resistant depression. Lancet 348:233–7.

Paus T (1996) Location and function of the human frontal eye field: a selective review. Neuropsychologia 34: 475–483.

Paus T, Jech R, Thompson C J, Comeau R, Peters T, Evans A C. (1997) Transcranial magnetic stimulation during positron emission tomography: a new method for studying connectivity of the human cerebral cortex. J Neurosci 17:3178–3184.

Pelizzari C A, Chen G T Y, Spelbring D R, Weichselbaum R R, Chen C T (1989). Accurate three-dimensionsl registration of CT, PET, and/or MRI images of the brain. *J Comput Assist Tomogr* 13:20–26.

Penfiled W, Roberts L (1959) Speech and Brain-Mechanisms. Princeton University Press, Princeton, N.J.

Pliszka, S. R, Liotti, M., Woldorff, M. G. (1998) Event-related potentials measured during a task assessing inhibitory control: Children with ADHD vs. Controls. *Proceedings of the Annual Meeting of the American Academy of Child Neurology*, in press.

Powers W, Fox P T, Raichle M E (1988) The effect of carotid artery disease on the cerebrovascular response to physiological stimulation. Neurology 38: 1475–1478.

Purpura, D P and McMurty J G (1965) Intracellular activities and evoked potential changes during polarization of motor cortex. J Neurophysiol 28:166–185.

Rank J B. (1975) Which Elements are excited in electrical stimulations of mamalian central nervous system: A review. Brain Research 98:417–440.

Rosenthal J, Waller H J, and Amassian V E. (1967) An analysis of the activation of motor cortical neurons by surface stimulation. J Neurophysiol 30:844–858.

Roth B J, Saypol J M, Hallet M, Cohen L G. (1991) A theoretical calculation of the electric field induced in the cortex during magnetic stimulation. Electroencephalography and clinical Neurophysiology18:47–56

Rudin D O and Eisenman G. (1954) The action potential of spinal axon in vitro, J Gen Physiol 37:505–538.

Rushton W A H. (1927) Effect upon the threshold for nervous excitation of the length of nerve explose and the angle between current and nerve. J Physiol 63:357–377.

Russ J R (1994). The Image Processing Handbook, 2nd Ed., CRC Press, Boca Raton, Fla.

Sastry B R, Goh J W, Auyeung A. (1986) Associative induction of posttetanic and long-term potentiation in CA1 neurons of rat hippocampus. Science 232:988–990.

Schroeder W, Martin K, Lorensen B (1996). *The visualization toolkit: An object-oriented approach to 3D graphics.* Prentice Hall, Upper Saddle River, N.J., pp. 146–152.

Sil'kis I G, Rapoport S, Veber N V, et al. (1994) Neurobiology of the integrative activity of the brain: some properties of long-term posttetanic heterosynaptic depression in the motor cortex of the cat. Neurosci.Behav.Physiol. 24:500–506.

Strother S C, Anderson J R, Xu X L, Liaw J S, Bonar D C, Rottenberg D A (1994). Quantitative comparisons of image registration techniques based on high-resolution MRI of the brain. *JCAT* 18(6):954–962.

Sturdivant V R, Wenzel D J, Seida S B (1995). Telerobot control using stereoscopic video. *Proceedings of the American Nuclear Society Sixth Topical Meeting on Robotics and Remote Systems*, Monterey, Calif., February.

Talairach J, Tournoux P (1988) Coplanar stereotactic atlas of the human brain: 3-dimensional proportional system: an approach to cerebral imaging. Stuttgart: Verlag.

Thompson W P. (1910) A physiological effect of an alternating magnetic field. proc R Soc Ser B 82:396–398.

Tofts P S and Branston N M (1991) The Measurement of electric field, and the influence of surface charge, in magnetic stimulation. Electroencephalography and Clinical Neurophysiology, 81:238–239.

Tokunaga A, Takase, Otani K. (1977) The glabella-inion line as a baseline for CT scanning of the brain. Neuroradiology 14: 67–71.

Trachina D, Nicholson C. (1986) A model for the polarization of neurons by extrinsically applied electric fields. Biophysical Journal 50:1139–1156.

Wada J, Rasmussen T. (1960) Intracarotid injection of sodium amytal for the lateralization of cerebral speech dominance: experimental and clinical observations. J Neurosurg 17:266–282.

Wada J A (1949) A new method for the determination of the side of cerebral speech dominance. A preliminary report on the intracarotid injection of sodium amytal in man. Igaku to Seibutsugaku 14:221–222 (in Japanese)

Wang H, Wang X, Scheich H. (1996) LTD and LTP induced by transcranial magnetic stimulation in auditory cortex. NeuroReport 7: 521–525.

Wasserman E M, Grafman, J., Berry, C., Hollnagel, C., Wild, K., Clark, K., & Hallett, M. (1996) Use and safety of a new repetitive transcranial magnetic stimulator. Electroencephalography and Clinical Neurophysiology 101, 412–417.

Wassermann, E M, Wang B, Zeffiro T, Sadato N, Pascual-Leone A, Toro C, Hallet M. 1996 Locating the motor cortex on the MRI with transcranial magnetic stimulation and PET. Neuroimage 3:1–9.

Weiss, S. R. B., Li, X. L., Rosen, J. B., Li, H., Heynen, T. & Post, R. M. (1995). Quenching: Inhibition of development and expression of amygdala kindled seizures with low frequency stimulation. NeuroReport 6, 2171–2176.

Wenzel D J, Seida S B, Sturdivant V R (1994). Telerobot control using enhanced stereo viewing. *Proceedings of the SPIE Conference on Telemanipulator and Telepresence Technologies*, Boston, Mass., October.

Woldorff, M. G., Fox, P. T., Matzke et 1 (1997) Retinotopic organization of early visual spatial attention effects as revealed by PET and ERPs. *Human Brain Mapping*, 5: 280–286, 1997.

Woldorff, M. G., Pridgen, S. C., Liotti, M., Rao, S., Perez III, R., Fox, P. T. (1998) The verb generation task: The timing of activations. *Proceedings of the Annual Meeting of the Society for Functional Brain Mapping*, in press.

Xiong J, Parsons L M, Pu Y, Gao J -H, Fox P T (1998) Covarying activity during rest reveals improved connectivity maps. NeuroImage: in press.

Xiong J, Rao S, Gao J -H, et al. (1998) Evaluation of hemispheric dominance for language using functional MRI: A comparison with positron emission tomography. Human Brain Mapping 6:42–58.

Yeomans X. Principles of Brain Stimulation. 1990.

What is claimed is:

1. A system for transcranial magnetic stimulation, comprising:
    a robotic member having a distal portion and a proximal portion, said robotic member having at least six degrees of freedom;
    a coil for generating an electric field, said coil coupled to said distal portion of said robotic member;
    a computer to control movement of said robotic member to position said coil at a preselected position relative to a subject according to a pre-specified treatment plan for magnetic stimulation in accordance with an aiming principle; and
    a storage coupled to the computer and storing the pre-specified treatment plan.

2. The system of claim 1, further comprising a power supply to supply energy to said coil to generate said electric field, said power supply comprising a capacitor bank.

3. The system of claim 1, further comprising a digitizer adapted to said robotic member.

4. A system comprising:
    a robotic arm having a distal end and a proximal end;
    a magnetic stimulator coupled to the distal end of the robotic arm;
    a controller coupled to the robotic arm to execute instructions; and
    a controller-readable medium coupled to the controller including instructions to control positioning of the magnetic stimulator according to a pre-specified treatment plan for magnetic stimulation in accordance with an aiming principle, the pre-specified treatment plan stored in the controller-readable medium.

5. The system of claim 4, wherein the robotic arm is capable of movement with at least six degrees of freedom.

6. The system of claim 5, wherein the robotic arm comprises at least five joints and a holder to hold the magnetic stimulator.

7. The system of claim 6, wherein the holder is adapted to hold the magnetic stimulator at least a first distance away from the robotic arm.

8. The system of claim 6, wherein the holder comprises a proximal portion coupled to the robotic arm and a distal portion coupled to the magnetic stimulator, wherein the holder comprises the sixth degree of freedom.

9. The system of claim 4, wherein the magnetic stimulator is rotatable about an axis.

10. The system of claim 4, further comprising a sensor to obtain information regarding orientation of the magnetic stimulator.

11. The system of claim 4, wherein the controller-readable medium further comprises instructions that enable the controller to move the magnetic stimulator to a predetermined position with respect to a subject via movement of the robotic arm without user involvement.

12. The system of claim 4, wherein the controller-readable medium further comprises instructions that enable the controller to move the magnetic stimulator to a plurality of predetermined sites with respect to a subject via movement of the robotic arm without user involvement.

13. The system of claim 4, wherein the robotic arm comprises a medical robot.

14. A system comprising:
- an active member capable of movement under machine control, the active member having a distal portion and a proximal portion;
- a transcranial magnetic stimulator coupled to the distal portion of the active member to provide magnetic stimulation to a subject;
- a controller coupled to the active member to execute instructions; and
- a controller-readable medium coupled to the controller including instructions to control positioning of the transcranial magnetic stimulator in accordance with a predetermined treatment plan for transcranial magnetic stimulation.

15. The system of claim 14, wherein the active member is capable of movement with at least six degrees of freedom.

16. The system of claim 14, wherein the controller-readable medium further comprises instructions that if executed enable the controller to move the transcranial magnetic stimulator to a predetermined position with respect to the subject via movement of the active member.

17. The system of claim 14, wherein the controller-readable medium further comprises instructions that if executed enable the controller to move the transcranial magnetic stimulator to a plurality of sites with respect to the subject via movement of the active member.

18. The system of claim 14, wherein the controller-readable medium further comprises instructions that if executed enable the controller to move the transcranial magnetic stimulator within a coordinate system corresponding to the predetermined treatment plan via movement of the active member.

19. A system comprising:
- a moveable member having a distal end and a proximal end, wherein the moveable member is capable of movement with six degrees of freedom;
- a magnetic stimulator coupled to the distal end of the moveable member;
- a controller coupled to the moveable member to control positioning of the magnetic stimulator in response to instructions; and
- a controller-readable medium coupled to the controller including instructions to control the positioning of the magnetic stimulator to a predetermined position with respect to a subject via movement of the moveable member in accordance with a pre-specified treatment plan for magnetic stimulation.

20. The system of claim 19, wherein the controller-readable medium further comprises instructions that if executed enable the controller to move the magnetic stimulator to a plurality of sites with respect to the subject via movement of the moveable member in accordance with the pre-specified treatment plan.

21. The system of claim 11, wherein the predetermined position comprises a brain location identified via an imaging procedure.

22. The system of claim 16, wherein the predetermined position comprises a brain location identified via an imaging procedure.

23. The system of claim 4, wherein the pre-specified treatment plan to position the magnetic simulator according to a cortical column cosine aiming principle.

24. The system of claim 1, wherein the pre-specified treatment plan to position the coil according to a cortical column cosine aiming principle.

25. The system of claim 14, wherein the predetermined treatment plan to position the transcranial magnetic simulator according to a cortical column cosine aiming principle.

* * * * *